US007927871B2

(12) United States Patent
Packard et al.

(10) Patent No.: US 7,927,871 B2
(45) Date of Patent: Apr. 19, 2011

(54) VISUALIZATION AND QUANTITATION OF CELLULAR CYTOTOXICITY USING CELL-PERMEABLE FLUOROGENIC PROTEASE SUBSTRATES AND CASPASE ACTIVITY INDICATOR MARKERS

(75) Inventors: Beverly Packard, Potomac, MD (US); Akira Komoriya, Rockville, MD (US)

(73) Assignee: Oncoimmunin, Inc., Gaithersburg, MD (US)

( * ) Notice: Subject to any disclaimer, the term of this patent is extended or adjusted under 35 U.S.C. 154(b) by 376 days.

(21) Appl. No.: 11/669,080

(22) Filed: Jan. 30, 2007

(65) Prior Publication Data

US 2007/0184493 A1 Aug. 9, 2007

Related U.S. Application Data

(63) Continuation-in-part of application No. 10/353,791, filed on Jan. 28, 2003, now abandoned.

(60) Provisional application No. 60/763,804, filed on Jan. 30, 2006, provisional application No. 60/353,712, filed on Jan. 29, 2002.

(51) Int. Cl.
*C12N 5/00* (2006.01)
*C12Q 1/37* (2006.01)
*G01N 33/53* (2006.01)

(52) U.S. Cl. .......................... 435/325; 435/7.72; 435/23

(58) Field of Classification Search .................. None
See application file for complete search history.

(56) References Cited

U.S. PATENT DOCUMENTS

| | | | |
|---|---|---|---|
| 5,605,809 | A | 2/1997 | Komoriya et al. |
| 5,714,342 | A | 2/1998 | Komoriya et al. |
| 6,037,137 | A | 3/2000 | Komoriya et al. |
| 6,248,904 | B1 | 6/2001 | Zhang et al. |
| 6,251,614 | B1 | 6/2001 | Fritz et al. |
| 6,270,980 | B1 | 8/2001 | Fritz et al. |
| 6,348,185 | B1 | 2/2002 | Piwnica-Worms |
| 6,391,575 | B1 | 5/2002 | Fritz et al. |
| 6,395,889 | B1 | 5/2002 | Robison |
| 6,759,207 | B2 | 7/2004 | Weber et al. |
| 2002/0055823 | A1 | 5/2002 | Kodaira |
| 2003/0211548 | A1 | 11/2003 | Packard et al. |

FOREIGN PATENT DOCUMENTS

| | | |
|---|---|---|
| WO | WO 98/37226 | 8/1998 |
| WO | WO 01/18238 | 3/2001 |
| WO | WO 03/084333 | 10/2003 |

OTHER PUBLICATIONS

Altman et al. (1996) "Phenotypic Analysis of Antigen-Specific T Lymphocytes", *Science* 274:94-96; erratum: 280:1821 (1998).
Appay et al. (2000) "HIV-specific CD8+ T Cells Produce Antiviral Cytokines but are Impaired in Cytolytic Function", *J. Exp. Med.* 192(1):63-75.
Bedner et al. (2000) "Activation of Caspases Measured in Situ by Binding of Fluorochrome-Labeled Inhibitors of Caspases (FLICA): Correlation with DNA Fragmentation", *Experimental Cell Research* 259:308-313.
Brunner et al. (1968) "Quantitative Assay of the Lytic Action of Immune Lymphoid Cells on $^{51}$Cr-Labelled Allogeneic Target Cells In vitro; Inhibition by Isoantibody and by Drugs", *Immunology* 14:181-196.
Butz et al. (1998) "Massive Expansion of Antigen-Specific CD8+ T Cells During an Acute Virus Infection", *Immunity*, 8:167-175.
Derby et al. (2001) "Three-color flow cytometric assay for the study of the mechanisms of cell-mediated cytotoxicity", *Immunology Letters* 78:35-39.
Doherty et al. (2000) "Accessing Complexity: The Dynamics of Virus-Specific T Cell Responses", *Annu. Rev. Immunol.* 18:561-592.
Komoriya et al. (2000) "Assessment of Caspase Activities in Intact Apoptotic Thymocytes Using Cell-permeable Fluorogenic Caspase Substrates", *J. Exp. Med.* 191(11):1819-1828.
Kottke et al. (2002) "Lack of Correlation between Caspase Activation and Caspase Activity Assays in Paclitaxel-treated MCF-7 Breast Cancer Cells*", *The J. Biol. Chem.* 277: 804-815.
Lecoeur et al. (2001) "A novel flow cytometric assay for quantitation and multiparametric characterization of cell-mediated cytotoxicity", *J. Immunol. Meth.* 253:177-187.
Lee et al. (1999) "Characterization of circulating T cells specific for tumor-associated antigens in melanoma patients", *Nature Med.* 5(6):677-685.
Liu et al. (2002) "Visualization and quantification of T cell-mediated cytotoxicity using cell-permeable fluorogenic caspase substrates", *Nature Med.* 8(2):185-189.
Maino et al. (1998) "Identification of Functional Subsets by Flow Cytometry: Intracellular Detection of Cytokine Expression", *Cytometry* 34:207-215.
Nociari et al. (1998) "A novel one step, highly sensitive fluorometric assay to evaluate cell-mediated cytotoxicity", *J. Immunol. Meth.* 213:157-167.
Packard et al. (1996) "Profluorescent protease substrates: Intramolecular dimers described by the exciton model", *PNAS USA* 93:11640-11645.

(Continued)

*Primary Examiner* — Marianne P Allen
(74) *Attorney, Agent, or Firm* — Weaver Austin Villeneuve & Sampson LLP; Tom Hunter

(57) ABSTRACT

This invention provides a non-radioactive assay to monitor and quantify the target-cell killing activities mediated by cytotoxic T lymphocytes (CTLs). This assay is predicated on the discovery that apoptosis pathway activation and, in particular, granzyme B activity, provides a measure of cytotoxic effector cell activity. In one embodiment, measurement of CTL-induced granzyme B activation in target cells is achieved through detection of the specific cleavage of fluorogenic granzyme B substrates. This assay reliably detects antigen-specific CTL killing of target cells, and provides a more sensitive, more informative and safer alternative to the standard $^{51}$Cr-release assay most often used to quantify CTL responses. The assay can be used to study CTL-mediated killing of primary host target cells of different cell lineages, and enables the study of antigen-specific cellular immune responses in real time at the single-cell level. As such, the assay can provide a valuable tool for studies of infectious disease pathogenesis and development of new vaccines and immunotherapies.

35 Claims, 8 Drawing Sheets

OTHER PUBLICATIONS

Packard et al. (2001) "Caspase 8 Activity in Membrane Blebs After Anti-Fas Ligation", *Journal of Immunology* 167:5061-5066.

Sarin et al. (1998) "Capase Dependence of Target Cell Damage Induced by Cytotoxic Lymphocytes", *The Journal of Immunology*, 161:2810-2816.

Sheehy et al. (2001) "A Novel Technique for the Fluorometric Assessment of T Lymphocyte Antigen Specific Lysis", *J. Immunol. Meth.* 249:99-110: erratum 252: 219-220 (2001).

Zajac et al. (1998) "Viral Immune Evasion Due to Persistence of Activated T Cells Without Effector Function", *J. Exp. Med*: 188(12):2205-2213.

GranToxiLux®: Fluorescence-based Cellular Cytotoxicity Assay

SEQUENCE LISTING

<160> NUMBER OF SEQ ID NOS: 37

<210> SEQ ID NO 1
<211> LENGTH: 18
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 1

Lys Asp Pro Xaa Gly Asp Glu Val Asp Gly Ile Asp Gly Xaa Pro Lys
1               5                   10                  15

Gly Tyr

<210> SEQ ID NO 2
<211> LENGTH: 18
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 2

Lys Asp Pro Xaa Gly Asp Glu Val Asp Gly Ile Asn Gly Xaa Pro Lys
1               5                   10                  15

Gly Tyr

<210> SEQ ID NO 3
<211> LENGTH: 18
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:

```
<221> NAME/KEY: misc_feature
<222> LOCATION: (14)..(14)
<223> OTHER INFORMATION: Xaa can be any naturally occurring amino acid

<400> SEQUENCE: 3

Lys Asp Pro Xaa Gly Leu Val Glu Ile Asp Asn Gly Gly Xaa Pro Lys
1               5                   10                  15

Gly Tyr

<210> SEQ ID NO 4
<211> LENGTH: 17
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (13)..(13)
<223> OTHER INFORMATION: Xaa can be any naturally occurring amino acid

<400> SEQUENCE: 4

Lys Asp Pro Xaa Tyr Val His Asp Ala Pro Val Gly Xaa Pro Lys Gly
1               5                   10                  15

Tyr

<210> SEQ ID NO 5
<211> LENGTH: 18
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 5

Lys Asp Pro Xaa Gly Tyr Val His Asp Gly Ile Asn Gly Xaa Pro Lys
1               5                   10                  15

Gly Tyr

<210> SEQ ID NO 6
<211> LENGTH: 18
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 6

Lys Asp Pro Xaa Gly Tyr Val Ala Asp Gly Ile Asn Gly Xaa Pro Lys
1               5                   10                  15
```

```
<210> SEQ ID NO 7
<211> LENGTH: 17
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (13)..(13)
<223> OTHER INFORMATION: Xaa can be any naturally occurring amino acid

<400> SEQUENCE: 7

Lys Asp Pro Xaa Ile Glu Thr Asp Ser Gly Val Gly Xaa Pro Lys Gly
1               5                   10                  15

Tyr

<210> SEQ ID NO 8
<211> LENGTH: 18
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 8

Lys Asp Pro Xaa Gly Leu Glu His Asp Gly Ile Asn Gly Xaa Pro Lys
1               5                   10                  15

Gly Tyr

<210> SEQ ID NO 9
<211> LENGTH: 15
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (11)..(11)
<223> OTHER INFORMATION: Xaa can be any naturally occurring amino acid

<400> SEQUENCE: 9

Lys Asp Pro Xaa Gly Ile Glu Pro Asp Gly Xaa Pro Lys Gly Tyr
1               5                   10                  15

<210> SEQ ID NO 10
<211> LENGTH: 18
<212> TYPE: PRT
<213> ORGANISM: Artificial
<220> FEATURE:
<223> OTHER INFORMATION: Synthetic protease substrate.
```

```
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 10

Lys Asp Pro Xaa Gly Ile Glu Pro Asp Gly Ile Asn Gly Xaa Pro Lys
1               5                   10                  15

Gly Tyr

<210> SEQ ID NO 11
<211> LENGTH: 18
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (14)..(14)
<223> OTHER INFORMATION: Xaa can be any naturally occurring amino acid

<400> SEQUENCE: 11

Lys Asp Pro Xaa Gly Ile Glu Thr Asp Gly Ile Asn Gly Xaa Pro Lys
1               5                   10                  15

Gly Tyr

<210> SEQ ID NO 12
<211> LENGTH: 16
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (12)..(12)
<223> OTHER INFORMATION: Xaa can be any naturally occurring amino acid

<400> SEQUENCE: 12

Lys Asp Pro Xaa Gly Ile Glu Pro Asp Ser Gly Xaa Pro Lys Gly Tyr
1               5                   10                  15

<210> SEQ ID NO 13
<211> LENGTH: 19
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (1)..(1)
<223> OTHER INFORMATION: Xaa is an S-t-butylthio-L-Cysteine residue..
<220> FEATURE:
<221> NAME/KEY: misc_feature
<222> LOCATION: (5)..(5)
<223> OTHER INFORMATION: Xaa is a 6-aminohexanoic acid residue or an
      epsilon-aminocaproic acid residue.
<220> FEATURE:
```

```
<221> NAME/KEY: misc_feature
<222> LOCATION: (15)..(15)
<223> OTHER INFORMATION: Xaa can be any naturally occurring amino acid

<400> SEQUENCE: 13

Xaa Lys Asp Pro Xaa Ser Val Gly Pro Asp Phe Gly Arg Gly Xaa Pro
1               5                   10                  15

Lys Gly Tyr

<210> SEQ ID NO 14
<211> LENGTH: 19
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (5)..(5)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (15)..(15)
<223> OTHER INFORMATION: Xaa can be any naturally occurring amino acid

<400> SEQUENCE: 14

Gly Lys Asp Pro Xaa Ser Val Gly Pro Asp Phe Gly Arg Gly Xaa Pro
1               5                   10                  15

Lys Gly Tyr

<210> SEQ ID NO 15
<211> LENGTH: 20
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (5)..(5)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (15)..(15)
<223> OTHER INFORMATION: Xaa can be any naturally occurring amino acid

<400> SEQUENCE: 15

Asp Lys Asp Pro Xaa Ser Val Gly Pro Asp Phe Gly Arg Gly Xaa Pro
1               5                   10                  15

Lys Asp Asp Gly
            20

<210> SEQ ID NO 16
<211> LENGTH: 22
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (7)..(7)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (17)..(17)
<223> OTHER INFORMATION: Xaa can be any naturally occurring amino acid

<400> SEQUENCE: 16

Glu Asp Gly Lys Asp Pro Xaa Ser Val Gly Pro Asp Phe Gly Arg Gly
```

-continued

```
                1               5                  10                 15
Xaa Pro Lys Asp Asp Gly
            20

<210> SEQ ID NO 17
<211> LENGTH: 20
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (5)..(5)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (15)..(15)
<223> OTHER INFORMATION: Xaa can be any naturally occurring amino acid

<400> SEQUENCE: 17

Lys Lys Asp Pro Xaa Ser Val Gly Pro Asp Phe Gly Arg Gly Xaa Pro
1               5                  10                 15

Lys Asp Asp Gly
            20

<210> SEQ ID NO 18
<211> LENGTH: 21
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (6)..(6)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (16)..(16)
<223> OTHER INFORMATION: Xaa can be any naturally occurring amino acid

<400> SEQUENCE: 18

Lys Lys Lys Asp Pro Xaa Ser Val Gly Pro Asp Phe Gly Arg Gly Xaa
1               5                  10                 15

Pro Lys Asp Asp Gly
            20

<210> SEQ ID NO 19
<211> LENGTH: 19
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (15)..(15)
<223> OTHER INFORMATION: Xaa can be any naturally occurring amino acid

<400> SEQUENCE: 19

Lys Asp Pro Xaa Gly Ser Val Gly Pro Asp Phe Gly Arg Gly Xaa Pro
1               5                  10                 15

Lys Gly Tyr
```

```
<210> SEQ ID NO 20
<211> LENGTH: 20
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (1)..(1)
<223> OTHER INFORMATION: Xaa is an S-t-butylthio-L-Cysteine residue.
<220> FEATURE:
<221> NAME/KEY: misc_feature
<222> LOCATION: (5)..(5)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (16)..(16)
<223> OTHER INFORMATION: Xaa can be any naturally occurring amino acid

<400> SEQUENCE: 20

Xaa Lys Asp Pro Xaa Gly Ser Val Gly Pro Asp Phe Gly Arg Gly Xaa
1               5                   10                  15

Pro Lys Gly Tyr
            20

<210> SEQ ID NO 21
<211> LENGTH: 20
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (5)..(5)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (16)..(16)
<223> OTHER INFORMATION: Xaa can be any naturally occurring amino acid

<400> SEQUENCE: 21

Gly Lys Asp Pro Xaa Gly Ser Val Gly Pro Asp Phe Gly Arg Gly Xaa
1               5                   10                  15

Pro Lys Gly Tyr
            20

<210> SEQ ID NO 22
<211> LENGTH: 4
<212> TYPE: PRT
<213> ORGANISM: Artificial
<220> FEATURE:
<223> OTHER INFORMATION: Synthetic protease substrate.

<400> SEQUENCE: 22

Asp Glu Val Asp
1

<210> SEQ ID NO 23
<211> LENGTH: 4
<212> TYPE: PRT
<213> ORGANISM: Artificial
<220> FEATURE:
<223> OTHER INFORMATION: Synthetic protease substrate.

<400> SEQUENCE: 23

Val Glu Ile Asp
1
```

```
<210> SEQ ID NO 24
<211> LENGTH: 4
<212> TYPE: PRT
<213> ORGANISM: Artificial
<220> FEATURE:
<223> OTHER INFORMATION: Synthetic protease substrate.

<400> SEQUENCE: 24

Asp Glu Val Asp
1

<210> SEQ ID NO 25
<211> LENGTH: 7
<212> TYPE: PRT
<213> ORGANISM: Artificial
<220> FEATURE:
<223> OTHER INFORMATION: Synthetic protease substrate.

<400> SEQUENCE: 25

Val Gly Pro Asp Phe Gly Arg
1               5

<210> SEQ ID NO 26
<211> LENGTH: 7
<212> TYPE: PRT
<213> ORGANISM: Artificial
<220> FEATURE:
<223> OTHER INFORMATION: Synthetic protease substrate.

<400> SEQUENCE: 26

Asp Glu Val Asp Gly Ile Asn
1               5

<210> SEQ ID NO 27
<211> LENGTH: 5
<212> TYPE: PRT
<213> ORGANISM: Artificial
<220> FEATURE:
<223> OTHER INFORMATION: Synthetic protease substrate.

<400> SEQUENCE: 27

Ile Glu Pro Asp Ser
1               5

<210> SEQ ID NO 28
<211> LENGTH: 4
<212> TYPE: PRT
<213> ORGANISM: Artificial
<220> FEATURE:
<223> OTHER INFORMATION: Synthetic protease substrate.

<400> SEQUENCE: 28

Ile Glu Pro Asp
1

<210> SEQ ID NO 29
<211> LENGTH: 4
<212> TYPE: PRT
<213> ORGANISM: Artificial
<220> FEATURE:
<223> OTHER INFORMATION: Synthetic protease substrate.

<400> SEQUENCE: 29

Val Gly Pro Asp
1

<210> SEQ ID NO 30
<211> LENGTH: 4
```

```
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (1)..(1)
<223> OTHER INFORMATION: Xaa is apspartyl
<220> FEATURE:
<221> NAME/KEY: misc_feature
<222> LOCATION: (2)..(2)
<223> OTHER INFORMATION: Xaa is glutanyl
<220> FEATURE:
<221> NAME/KEY: misc_feature
<222> LOCATION: (3)..(3)
<223> OTHER INFORMATION: Xaa is valyl
<220> FEATURE:
<221> NAME/KEY: misc_feature
<222> LOCATION: (4)..(4)
<223> OTHER INFORMATION: Xaa is aspartyl

<400> SEQUENCE: 30

Xaa Xaa Xaa Xaa
1

<210> SEQ ID NO 31
<211> LENGTH: 18
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (4)..(4)
<223> OTHER INFORMATION: Xaa is a 6-aminohexanoic acid residue or an
      epsilon-aminocaproic acid residue.
<220> FEATURE:
<221> NAME/KEY: misc_feature
<222> LOCATION: (13)..(13)
<223> OTHER INFORMATION: Xaa can be any naturally occurring amino acid

<400> SEQUENCE: 31

Lys Asp Pro Xaa Gly Asp Glu Val Asp Gly Ile Asp Xaa Gly Pro Lys
1               5                   10                  15

Gly Tyr

<210> SEQ ID NO 32
<211> LENGTH: 9
<212> TYPE: PRT
<213> ORGANISM: Artificial
<220> FEATURE:
<223> OTHER INFORMATION: Synthetic protease substrate.

<400> SEQUENCE: 32

Phe Gln Pro Gln Asn Gly Gln Phe Ile
1               5

<210> SEQ ID NO 33
<211> LENGTH: 9
<212> TYPE: PRT
<213> ORGANISM: Artificial
<220> FEATURE:
<223> OTHER INFORMATION: Synthetic protease substrate.

<400> SEQUENCE: 33

Lys Ala Val Tyr Asn Phe Ala Thr Cys
1               5

<210> SEQ ID NO 34
<211> LENGTH: 11
<212> TYPE: PRT
```

```
<213> ORGANISM: Artificial
<220> FEATURE:
<223> OTHER INFORMATION: Synthetic protease substrate.

<400> SEQUENCE: 34

Ser Gly Val Glu Asn Pro Gly Gly Tyr Cys Leu
1               5                   10

<210> SEQ ID NO 35
<211> LENGTH: 8
<212> TYPE: PRT
<213> ORGANISM: Artificial
<220> FEATURE:
<223> OTHER INFORMATION: Synthetic protease substrate.

<400> SEQUENCE: 35

Tyr Thr Val Lys Tyr Pro Asn Leu
1               5

<210> SEQ ID NO 36
<211> LENGTH: 8
<212> TYPE: PRT
<213> ORGANISM: Artificial
<220> FEATURE:
<223> OTHER INFORMATION: Synthetic protease substrate.

<400> SEQUENCE: 36

Ser Asn Pro Thr Tyr Ser Val Met
1               5

<210> SEQ ID NO 37
<211> LENGTH: 3
<212> TYPE: PRT
<213> ORGANISM: Artificial
<220> FEATURE:
<223> OTHER INFORMATION: Synthetic protease substrate.
<220> FEATURE:
<221> NAME/KEY: misc_feature
<222> LOCATION: (1)..(1)
<223> OTHER INFORMATION: Xaa is l-valyl
<220> FEATURE:
<221> NAME/KEY: misc_feature
<222> LOCATION: (2)..(2)
<223> OTHER INFORMATION: Xaa is -l-alanyl
<220> FEATURE:
<221> NAME/KEY: misc_feature
<222> LOCATION: (3)..(3)
<223> OTHER INFORMATION: Xaa is l-aspartyl

<400> SEQUENCE: 37

Xaa Xaa Xaa
1
```

VISUALIZATION AND QUANTITATION OF CELLULAR CYTOTOXICITY USING CELL-PERMEABLE FLUOROGENIC PROTEASE SUBSTRATES AND CASPASE ACTIVITY INDICATOR MARKERS

CROSS-REFERENCE TO RELATED APPLICATIONS

This application claims benefit of and priority to U.S. Ser. No. 60/763,804, filed on Jan. 30, 2006, which is incorporated herein by reference in its entirety for all purposes. This application is also a continuation-in-part of U.S. Ser. No. 10/353,791, filed Jan. 28, 2003, which claims benefit of and priority to U.S. Ser. No. 60/353,712, filed Jan. 29, 2002, all of which are herein incorporated by reference in their entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention pertains to the field of immunology. In particular, this invention provides improved cellular assays for determining the presence or activity of cytotoxic effectors cells that will mount a cytotoxic response against a particular cell or antigen including pathogen.

BACKGROUND OF THE INVENTION

Cytotoxic T lymphocytes (CTLs) have crucial roles in eliminating host cells that contain intracellular pathogens and those that have undergone malignant transformation (Doherty and Christensen (2000) Annu. Rev. Immunol. 18: 561-592). In the past three decades, the $^{51}$Cr-release assay has been used to quantify antigen-specific cell-mediated cytotoxicity activity (Brunner et al. (1968) Immunology 14: 181-196). In this assay, target cells labeled with radioactive $^{51}$Cr are incubated with effector cells for 4-6 hours. Target-cell death is then measured by detecting radioactivity released into the culture supernatant.

Although relatively reproducible and simple, this assay has numerous disadvantages (Doherty and Christensen (2000) Annu. Rev. Immunol. 18: 561-592). First, bulk cell-mediated cytotoxicity activity is measured using 'lytic unit' calculations that do not quantify target-cell death at the single-cell level. Second, CTL killing of primary host target cells often cannot be studied directly as only certain types of cells, primarily immortalized cell lines, can be efficiently labeled with $^{51}$Cr (Nociari et al. (1998) J. Immunol. Meth. 213: 157-167). Third, target-cell death is measured at the end point of the entire process and thus provides little information about the kinetic interaction of effectors and targets at the molecular and cellular levels. Fourth, the radio active conventional assay using chromium 51 isotope ($^{51}$Cr) results in a very large background (noise) signal due to a large amount of spontaneous nonspecific release of the isotope from the target cells and often very heterogeneous loading of the isotope in the selected target cells. Fifth, the amount of released radio activity is therefore not a direct measure of cell death but rather membrane permeability change and spontaneous release of the isotope from the loaded cells due to processes other than the cellular cytotoxicity brought about by the cytotoxic effector cells. Consequently, the conventional chromium release assay has difficulty in detecting definite but less potent cytotoxic effects, i.e., it is difficult to distinguish a signal caused by cell-mediated cytotoxic activity from the assay's background radioactivity. Measurement of $^{51}$Cr release does not permit monitoring the physiology or fate of effector cells as they initiate and execute the killing process. Finally, radioactive materials require special licensing and handling, which substantially increases cost and complexity of the assay.

More recently developed immunologic methods, including major histocompatibility complex (MHC)-tetramers, intracellular cytokine detection and ELISPOT assays, have greatly improved sensitivity to enumerate antigen-specific T cells; however, these newer methods do not assess the cytolytic function of antigen-specific cell-mediated cytotoxicity (Altman et al. (1996) Science, 274: 94-96 (1996); erratum: 280: 1821 (1998); Butz and Bevan (1998) Immunity 8:167-175; Maino and Picker (1998) Cytometry 34: 207-215). Given emerging data indicating that antigen-specific $CD8_+$ T cells may be present in certain chronic infections or malignancies, but blocked in their ability to lyse target cells, assays that measure all the effector cell functions at the single-cell level are needed (Appay et al. (2000) J. Exp. Med. 192: 63-75; Lee et al. (1999) Nature Med. 5: 677-685; Zajac et al. (1998) J. Exp. Med. 188: 2205-2213).

In recent efforts to overcome some of the limitations of the $^{51}$Cr-release assay through development of flow cytometry based cell-mediated cytotoxicity assays, some groups have measured target-cell death based on the amount of fluorochrome released from or retained in the prelabeled target cells (Sheehy et al. (2001) J. Immunol. Meth. 249: 99-110; erratum: 252: 219-220 (2001)), or detected the late stages of target-cell death using intercalative DNA dyes (Lecoeur et al. (2001) J. Immunol. Meth. 253: 177-187). However, none of these assays reveal the fundamental processes responsible for the initiation and execution of target-cell killing, and none have yet been applied to analyses of primary cell-mediated cytotoxicity generated in vivo following antigenic exposure.

SUMMARY OF THE INVENTION

This invention pertains to a novel non-radioactive assay that provides a measure of the existence and magnitude of a cell-mediated cytotoxic response against a particular target antigen and/or target cell. In particular, in certain embodiments, this invention pertains to the discovery that cell-mediated cytotoxicity, determined using non-radioactive intracellular caspase and/or granzyme (e.g., granzyme A and/or granzyme B) activity indicators or reporter molecules (particularly fluorescent or fluorogenic indicators) and, optionally, using flow cytometry as a single cell based detector show surprisingly high sensitivity. These assays can, for example, detect memory cell cytotoxic activity under conditions (e.g. at early time points, or extremely long after challenge where the memory activity is low) where the conventional radioactive chromium 51 release assay fails to effectively detect such activity.

This invention also pertains to the activation of an apoptosis pathway in the target cell (the cell that is killed) as cell-mediated cytotoxicity proceeds. Thus, detection of activity of an apoptosis pathway (e.g. caspase activity, nuclear disruption, Granzyme B activity etc.) in a target cell contacted with a cytotoxic effector cell (e.g. CTL, NK cell, macrophage, etc.) provides a more sensitive measure of cytotoxicity associated, e.g. with a minor antigen.

The non-radioactive assays of this invention are a good replacement of the traditional radioactive "chromium release" assay.

In certain embodiments, this invention provides a method of detecting cell-mediated cytotoxic activity. The method typically involves coincubating a target cell with a cytotoxic effector cell; and detecting the presence or activity of an activated caspase and/or granzyme B and/or other protease (e.g. various granule derived proteases) in the target cell where the presence or activity of the activated caspase and/or granzyme B and/or other protease is detected using a fluorescent or fluorogenic indicator of the presence or activity of an activated caspase and/or granzyme B and/or other protease, and where the presence or activity of the activated caspase and/or granzyme B and/or other protease indicates that the cytotoxic effector cell has been activated in the target cell. In certain embodiments, preferred cytotoxic effector cells include, but are not limited to a cytotoxic T lymphocyte (CTL), a natural killer (NK) cell, and a macrophage. In certain embodiments, the detecting comprises detecting one or more indicators in a single cell (e.g., utilizing a single cell image based instrument). In certain embodiments, the detecting does not utilize a cell sorter. In certain embodiments, the detecting comprises contacting cleavage products produced by the activated caspase and/or granzyme with a fluorescently labeled antibody that specifically binds the cleavage products and/or contacting a substrate for an activated caspase and/or granzyme with a fluorescently labeled antibody that specifically binds the substrate before or after it is cleaved by the caspase and/or granzyme B. In certain embodiments, the detecting comprises contacting a substrate for a cellular protein (e.g., PARP, nuclear lamin, DNA-PK, etc.) that is processed by a granule derived protease involved in apoptosis in target cells and/or detecting the newly generated cellular DNA fragments induced by apoptosis induced nuclease activities. In certain embodiments, the detecting comprises contacting the activated caspase and/or granzyme B with an indicator comprising a fluorescently labeled ligand that specifically binds to the activated caspase and/or granzyme B. Certain preferred fluorescent or fluorogenic ligands specifically bind to the substrate binding site of the activated caspase and/or granzyme. In certain embodiments, the ligand comprises a subsequence of a polypeptide selected from the group consisting of PARP, nuclear lamin, actin, PKC gamma, SREBP, U1-RNP, DNA-PK, G4-GDI, huntingtin, and HnRNP-C1/2, where the subsequence is of sufficient length (e.g. at least 1 amino acid, preferably at least 2 amino acids, more preferably at least 4, 6, or 8 amino acids) to specifically bind to the substrate binding site of the activated caspase and/or granzyme. Certain preferred activated caspases include, but are not limited to caspase-1, caspase-2, caspase-3, caspase-6, caspase-8, caspase-9, and caspase-10 and certain preferred granule-derived proteases including, but not limited to granzyme A and/or granzyme B. In certain embodiments, the ligand is an antibody that specifically binds an active caspase and/or granzymes. In certain embodiments, the ligand comprises a polypeptide that is a substrate for an active caspase and/or a granzyme. Certain preferred ligands include, but are not limited to, a ligand comprising an amino acid sequence selected from the group consisting of KDPC$_5$GDEVDGIDGC$_5$PKGY (SEQ ID NO:1), KDPC$_5$GDEVDGINGC$_5$PKGY (SEQ ID NO:2), KDPC$_5$GLVEIDNGGC$_5$PKGY (SEQ ID NO:3), KDPC$_5$YVHDAPVGC$_5$PKGY (SEQ ID NO:4), KDPC$_5$GYVHDGINGC$_5$PKGY (SEQ ID NO:5), KDPC$_5$GYVADGINGC$_5$PKGY (SEQ ID NO:6), KDPC$_5$IETDSGVGC$_5$PKGY (SEQ ID NO:7), KDPC$_5$GLEHDGINGC$_5$PKGY (SEQ ID NO:8), and KDPC$_5$GIEPDGC$_5$PKGY (SEQ ID NO:9), KDPC$_5$GIEPDGINGC$_5$PKGY (SEQ ID NO:10), and KDPC$_5$GIETDGINGC$_5$PKGY (SEQ ID NO:11) (see, e.g., U.S. Pat. Nos. 6,037,137; 5,605,809; 5,714,342; and PCT Publications WO 01/18238 and WO 98/37226, which are herein incorporated by reference in their entirety for all purposes), and KDPC$_5$GIEPDSGC$_5$PKGY (SEQ ID NO:12), C(S-t-Buthio)KDPC$_5$SVGPDFGRGC$_5$PKGY (SEQ ID NO:13), GKDPC$_5$SVGPDFGRGC$_5$PKGY (SEQ ID NO:14), DKDPC$_5$SVGPDFGRGC$_5$PKDDG (SEQ ID NO:15), EDGKDPC$_5$SVGPDFGRGC$_5$PKDDG (SEQ ID NO:16), KKDPC$_5$SVGPDFGRGC$_5$PKDDG (SEQ ID NO:17), KKKDPC$_5$SVGPDFGRGC$_5$PKDDG (SEQ ID NO:18), KDPC5GSVGPDFGRGC5PKGY (SEQ ID NO:19), C(S-tButhio)KDPC5GSVGPDFGRGC5PKGY (SEQ ID NO:20), and GKDPC5GSVGPDFGRGC5PKGY (SEQ ID NO:21) where C$_5$ is a 6-aminohexanoic acid residue or an epsilon-aminocaproic acid residue and C(S-t-Buthio) is a S-t-butylthio-L-Cysteine residue.

In certain embodiments, the ligand is attached to a single chromophore whose fluorescence signal or whose absorption spectrum is altered when the substrate is cleaved by the active caspase and/or granzyme. In certain embodiments, the ligand comprises a substrate for a caspase and/or granzyme B and in the amino terminal residue of the substrate is linked to the same fluorophore as the carboxyl terminus, while in other embodiments, the ligand is attached to two chromophores whose fluorescence signal or whose absorption spectra is altered when the substrate is cleaved by the active caspase or granzyme. The chromophores and ligand can be chosen so that the chromophores form an H-dimer, a J-dimer or so that they do not form either dimer. In certain instances, the chromophores comprise one non-fluorescent chromophore and a fluorophore. In certain instances the chromophores are both fluorophores and the same species of fluorophore. In certain embodiments, the ligand is a suicide inhibitor (e.g. an irreversible inhibitor) of an active caspase and/or granzyme B or a reversible inhibitor of an active caspase and/or granzyme B. Certain suicide inhibitors comprise a reactive including, but not limited to fluromethylketone, chroromethylketone, bromomethylketone and iodomethylketone.

In certain embodiments, the ligand comprises an aldehyde moiety in the P1' position. In certain embodiments, the ligand comprises a caspase substrate having a fluorophore or chromophore at a position ranging from P1' to a P8' residue. The amino and/or carboxyl terminal residue of the substrate can be blocked or unblocked. Certain preferred indicators comprise a fluorophore including but not limited to fluorosceine, phycoerythine, carboxytetramethylrhodamine, carboxyrhodamine-X, carboxyrhodamine 110, diethylaminocoumarin, and carbocyanine dyes. The indicator can bear one or more hydrophobic groups which can be a fluorophore, a chromophore or another hydrophobic group (e.g. Fluorenylmethoxycarbonyl (Fmoc), 9-fluoreneacetyl group (Fa), 1-fluorenecarboxylic group, 9-florenecarboxylic group, and 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4'-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), Benzyl (Bzl), benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), trifluoroacetyl (TFA), and the like). In certain instances, the indicator is within the target cell. In certain instances, the coincubating comprises lysing the target cell. In certain instances, the target and/or effector cells are in a histological section. In certain embodiments, the target cell contains caspase indicators specific for two or more different caspases and granzyme B and/or A indicator(s). The target cell can optionally be infected with a virus, a bacterium, or other microorganism and/or express one or more heterologous proteins. Preferred target cells include, but are not limited to a tumor cell, a neural cell, a muscle cell, a fibroblast, a connective tissue cell, a bone cell, a blood cell, a spinal fluid derived cell, a lymphatic fluid derived cell, and a cell obtained from the site of an inflammation.

In another embodiment, this invention provides a method of detecting cell-mediated cytotoxic activity. The method typically involves coincubating a target cell with a cytotoxic effector cell; and detecting the presence or activity of an activated caspase in the target cell where the presence or activity of the activated caspase indicates that the cytotoxic effector cell is active against the target cell. Preferred cytotoxic effector cells include, but are not limited to a cytotoxic T lymphocyte (CTL), a natural killer (NK) cell, and a macrophage. The detecting can involve any of the method and/or indicators described and/or claimed herein (see, e.g., description above). Similarly, the indicators can comprise any of the fluorophores, chromophores, ligand, protecting groups, hydrophobic groups and the like described or claimed herein. In certain instances, the indicator is within the target cell. In certain instances, the coincubating comprises lysing the target cell. In certain instances, the target and/or effector cells are in a histological section. In certain embodiments, the target cell contains caspase indicators specific for two or more different caspases. The target cell can optionally be infected with a virus, a bacterium, or other microorganism and/or express one or more heterologous proteins. Preferred target cells include, but are not limited to a tumor cell, a neural cell, a muscle cell, a fibroblast, a connective tissue cell, a bone cell, a blood cell, a spinal fluid derived cell, a lymphatic fluid derived cell, and a cell obtained from the site of an inflammation.

In still another embodiment, this invention provides a method of detecting cell-mediated cytotoxic activity. The method typically involves coincubating a target cell with a cytotoxic effector cell; and detecting activity of an apopotosis pathway in the target cell where activity of the apopotosis pathway indicates that the cytotoxic effector cell is active against the target cell. Preferred cytotoxic effector cells include, but are not limited to a cytotoxic T lymphocyte (CTL), a natural killer (NK) cell, and a macrophage. In certain embodiments, the detecting activity of an apopotosis pathway comprises detecting activity of a protease in an apopotosis pathway. In certain embodiments, the target cell comprises an indicator that provides a signal indicating the activity of a protease (e.g. an activated caspase) comprising an apopotosis pathway. In certain embodiments, the detecting activity of an apopotosis pathway comprises measuring activity or level of granzymes, cathepsin W, or calpain in the target cell. The activity or level of, e.g., granzyme A and B, cathepsin W, or calpain in the target cell can be determined by any of a number of methods including, but not limited to using an antibody specific to granzyme, cathepsin W, or calpain, capillary electrophoresis, mass spectroscopy, etc. In certain embodiments, the detecting activity of an apopotosis pathway comprises measuring nuclear fragmentation of the target cell. Nuclear fragmentation can be determined by any of a number of methods known to those of skill in the art. One method involves staining the nucleus of the target cell. In certain embodiments, the detecting activity of an apopotosis pathway comprises detecting binding of annexin-V (e.g., annexin-V labeled with a detectable label) to a target cell. In certain embodiments, the detecting activity of an apopotosis pathway comprises using an agent (e.g., PI, 7-ADD, and ethidium bromide, etc.) that preferentially or specifically stains cells with compromised or damaged plasma membranes.

This invention also provides a method of detecting the presence of memory cytotoxic effector activity. The method typically involves coincubating a target cell with a cytotoxic effector cell where the coincubating is at least 8 days (preferably at least 10 days, more preferably at least 15, 30, or 60 days) after initial stimulation with the immunogen against which the effector activity is directed; and/or; the cytotoxic effector cell is a memory cell; and detecting the presence or activity of an activated caspase in the target cell where the presence or activity of the activated caspase is detected using a fluorescent or fluorogenic indicator of the presence or activity of an activated caspase, and where the presence or activity of the activated caspase indicates that a memory cytotoxic effector cell is active against the target cell. In certain instances, the cytotoxic effector cell is a CD8+ T cell. In certain instances, the method does not involve re-stimulating the effector cell. The detecting can be by any of the methods described herein (e.g., using any one or more of the indicators described herein).

In still yet another embodiment, this invention provides a method of screening a test agent for the ability to induce in a mammal a class I-restricted CTL response directed against a particular antigen. The method typically involves administering to a mammal a test agent; obtaining an effector cell from the mammal; and measuring cytotoxic activity of the effector cell against a target displaying the antigen, where the cytotoxic activity is measured using any of the methods and/or indicators described herein, where cytotoxic activity of the effector cell against the target cell is an indicator that the test agent induces a class I-restricted CTL response directed against the antigen.

This invention also provides a method of optimizing an antigen for use in a vaccine. The method typically involves providing a plurality of antigens that are candidates for the vaccine; screening the antigens using any of the methods and/or indicators described herein; and selecting an antigen that induces a class I-restricted CTL response directed against the antigen.

Also provided is a method of testing a mammal to determine if the mammal retains immunity from a previous vaccination, immunization or disease exposure. The method typically involves obtaining an effector cell from the mammal; and measuring cytotoxic activity of the effector cell against a target cell displaying an antigen that is a target of an immune response induced by the vaccination, immunization, or disease exposure, where the cytotoxic activity is measured using any of the methods and/or indicators described herein, where cytotoxic activity of the effector cell against the target cell is an indicator that the animal retains immunity from the vaccination, immunization, or disease exposure. In certain embodiments, the effector cell is a cytotoxic T lymphocyte (CTL) (e.g. a CD8+ cytotoxic T lymphocyte).

In certain embodiments, this invention provides a method of testing a mammal to determine if the mammal has been exposed to a particular antigen. The method typically involves obtaining an effector cell from the mammal and measuring cytotoxic activity of the effector cell against a target cell displaying the antigen, where the cytotoxic activity is measured using the methods and/or indicators described herein, where cytotoxic activity of the effector cell against the target cell is an indicator that the animal has been exposed to the antigen.

In still yet another embodiment, this invention provides a method of testing a mammal to determine if the mammal will mount a cell-mediated immune response against an organ or tissue. The method typically involves obtaining an effector cell from the mammal; and measuring cytotoxic activity of the effector cell against a target cell derived from the organ or tissue, where the cytotoxic activity is measured using any of the methods and/or indicators described herein, where cytotoxic activity of the effector cell against the target cell is an indicator that the mammal will mount an immune response against the organ or tissue. In certain embodiments, the organ or tissue is heterologous organ or tissue that is a candidate for transplantation into the mammal.

Definitions

The following abbreviations are used herein: 7-AAD, 7-amino-actinomycin D; CTL, cytotoxic T lymphocytes; FC Assay, Flow Cytometric Cytotoxicity Assay; FCS, fetal calf serum; NK, natural killer cells; PBMC, peripheral blood mononuclear cells; PI, propidium iodide; PS, phosphatidylserine; rIL-2, recombinant human interleukin-2.

The symbol "$C_5$", when used in a peptide sequence indicates that the residue is a 6-aminohexanoic acid residue or an epsilon-aminocaproic acid residue. C(S-t-Buthio) is a S-t-butylthio-L-Cysteine residue.

A "suicide inhibitor" of a protease is a ligand that binds essentially irreversibly to a protease and typically thereby inhibits activity of said protease.

A memory cell refers to a cell that exhibits specific cellular cytotoxic activity beyond a defined time point, e.g., 8 days.

The term "coincubating" as used herein with respect to an effector and/or a target cell refers to placing the effector and/or target cell into a buffer and/or medium wherein the cells are capable of interacting (e.g. inducing a cytotoxic response). In certain embodiments, coincubating may involve heating, warming, or maintaining the cells at a particular temperature and/or passaging of the cells.

The term blocked when used with respect to a chemically reactive group (e.g. an alpha amino group on a peptide) indicates that the functional group is no longer substantially chemically reactive. The term unblocked indicates that the group is chemically reactive.

A "fluorescent indicator" refers to an indicator that is fluorescent, and a "fluorogenic indicator" refers to an indicator that that when modified (e.g. by interaction with its target molecule) alters (e.g. increases or decreases) its fluorescence.

A "J-dimer" refers to 2 fluorophores whose transition dipoles are arranged in a head to tail configuration resulting in a splitting of the excited singlet state; transitions between a ground state and an upper excited state are considered forbidden and transitions between a ground state a lower excited state allowed. An "H-dimer" refers to two fluorophores whose transition dipoles are arranged in a parallel configuration resulting in a splitting of the excited singlet state; transitions between a ground state and an upper excited state are considered allowed and transitions between a ground state a lower excited state forbidden.

A "a single cell image based instrument" is an instrument that permits imaging and/or processing of information from a single cell.

The term "protease binding site" is used herein to refer to an amino acid sequence that is characteristically recognized and cleaved by a protease. The protease binding site contains a peptide bond that is hydrolyzed by the protease and the amino acid residues joined by this peptide bond are said to form the cleavage site. These amino acids are designated $P_1$ and $P_1'$ for the residues on the amino and carboxyl sides of the hydrolyzed bond respectively.

A "chromophore" is a group, substructure, or molecule that is responsible for the absorption of light. Typical chromophores each have a characteristic absorption spectrum.

A "fluorophore" is a chromophore that absorbs light at a characteristic wavelength and then re-emits the light most typically at a characteristic different wavelength. Fluorophores are well known to those of skill in the art and include, but are not limited to rhodamine and rhodamine derivatives, fluorescein and fluorescein derivatives, coumarins and chelators with the lanthanide ion series. A fluorophore is distinguished from a chromophore which absorbs, but does not characteristically re-emit light.

A "fluorogenic indicator" or "fluorogenic composition" is an indicator (indicator composition) of this invention that produces a fluorescent signal.

A "protease indicator" is a composition that indicates the presence or activity of a protease. More preferably a protease indicator is a composition that indicates the presence or activity of protease activity.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose α carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

The polypeptides described herein are preferably written with the amino terminus at the left and the carboxyl terminus at the right. The amino acids comprising the peptide components of this invention are numbered with respect to the protease cleavage site, with numbers increasing consecutively with distance in both the carboxyl and amino direction from the cleavage site. Residues on the carboxyl site are either notated with a "'" as in $P_1'$, or with a letter and superscript indicating the region in which they are located. The "'" indicates that residues are located on the carboxyl side of the cleavage site.

The term "residue" or "amino acid" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "domain" or "region" refers to a characteristic region of a polypeptide. The domain may be characterized by a particular structural feature such as a β turn, an alpha helix, or a β pleated sheet, by characteristic constituent amino acids (e.g. predominantly hydrophobic or hydrophilic amino acids, or repeating amino acid sequences), or by its localization in a particular region of the folded three dimensional polypeptide. As used herein, a region or domain is composed of a series of contiguous amino acids.

The terms "protease activity" or "activity of a protease" refer to the cleavage of a peptide by a protease. Protease activity comprises the "digestion" of one or more peptides into a larger number of smaller peptide fragments. Protease activity of particular proteases may result in hydrolysis at particular peptide binding sites characteristically recognized by a particular protease. The particular protease may be characterized by the production of peptide fragments bearing particular terminal amino acid residues.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 3000 Da, more preferably up to 2000 Da, and most preferably up to about 1000 Da.

The term macromolecule refers to a "large" molecule. Biopolymers (e.g. proteins, glycoproteins, carbohydrates, lipids, polysaccharides, and the like) are typical macromolecules. Typical macromolecules have a molecular weight greater than about 1000 Da, preferably greater than about 2000 Da, more preferably greater than about 3000 Da, and most preferably greater than about 4,000 or 5,000 Da.

The term "biological sample", as used herein, refers to a sample obtained from an organism, from components (e.g., cells or tissues) of an organism, and/or from in vitro cell or tissue cultures. The sample may be of any biological tissue or fluid (e.g. blood, serum, lymph, cerebrospinal fluid, urine, sputum, etc.). Biological samples can also include whole organisms, organs or sections of tissues such as frozen sections taken for histological purposes.

The term "specifically binds", when referring to the interaction of a nucleic acid binding protein and a nucleic acid binding site or two proteins or other binding pairs refers to a binding reaction which is determinative of the presence of the one or other member of the binding pair in the presence of a heterogeneous population of molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, etc. The binding may be by one or more of a variety of mechanisms including, but not limited to ionic interactions, covalent interactions, hydrophobic interactions, van der Waals interactions, etc. A molecule that "specifically binds" the active form of a protease (e.g. a protease) is preferably capable of distinguishing the active form of the protease from the inactive "pro" form of the protease.

The terms "binding partner", or a member of a "binding pair", or "cognate ligand" refers to molecules that specifically bind other molecules to form a binding complex such as antibody/antigen, lectin/carbohydrate, nucleic acid/nucleic acid, receptor/receptor ligand (e.g. IL-4 receptor and IL-4), avidin/biotin, etc.

The term ligand is used to refer to a molecule that specifically binds to (e.g. covalently or noncovalently forms a complex with) another molecule. Commonly a ligand is a soluble molecule, e.g. a hormone or cytokine, that binds to a receptor. The decision as to which member of a binding pair is the ligand and which the "receptor" is often a little arbitrary when the broader sense of receptor is used (e.g., where there is no implication of transduction of signal). In these cases, typically the smaller of the two members of the binding pair is called the ligand. Thus, for example in a lectin-sugar interaction, the sugar would be the ligand (even if it is attached to a much larger molecule, recognition is of the saccharide), in a protease substrate interaction, the substrate (the molecule bound and/or cleaved by the protease) can be considered a ligand, and so forth.

The term "target cell" refers to a cell against which the activity of a cytotoxic effector cell is tested. Preferred target cells can display one or more than one antigen.

The term "effector cell" or "cytotoxic effector cell" refers to a cell that is capable of killing or directly or indirectly bringing about the death of a target cell displaying an antigen against which the effector cell is directed. Preferred effector cells include, but are not limited to cytotoxic T lymphocytes (CTLs), natural killer (NK) cells, and macrophages.

Two fluorophores are said to quench each other in an H-dimer when their aggregate fluorescence in an H-dimer formation is detectably less than the aggregate fluorescence of the fluorophores when they are separated (e.g. in solution at approximately 10 µM or less). The absorption maximum of an H-dimer absorption spectrum as compared with spectrum of the individual fluorophores composing the H-dimer shows the maximum absorption wavelength to be shifted to a shorter wavelength. In contrast, the absorption spectrum of a J-dimer as compared with the spectrum of the individual fluorophores composing the J-dimer shows the maximum absorption wavelength to be shifted to a longer wavelength. Fluorescence intensity of H-dimers or aggregates exhibits an intensity less than those of its components whereas the fluorescence intensity of the J-dimer or aggregate exhibits equal or greater fluorescence intensity than their components alone. Either an increase or decrease in fluorescence intensity behavior of the H- or J-dimer molecules or aggregates can be utilized as an indicator of a molecule's signal reporter moiety. In preferred embodiments the fluorophores increase or quench by at least 50%, preferably by at least 70%, more preferably by at least 80%, and most preferably by at least 90%, 95%, or even at least 99%.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331).

DETAILED DESCRIPTION

Figure 1:
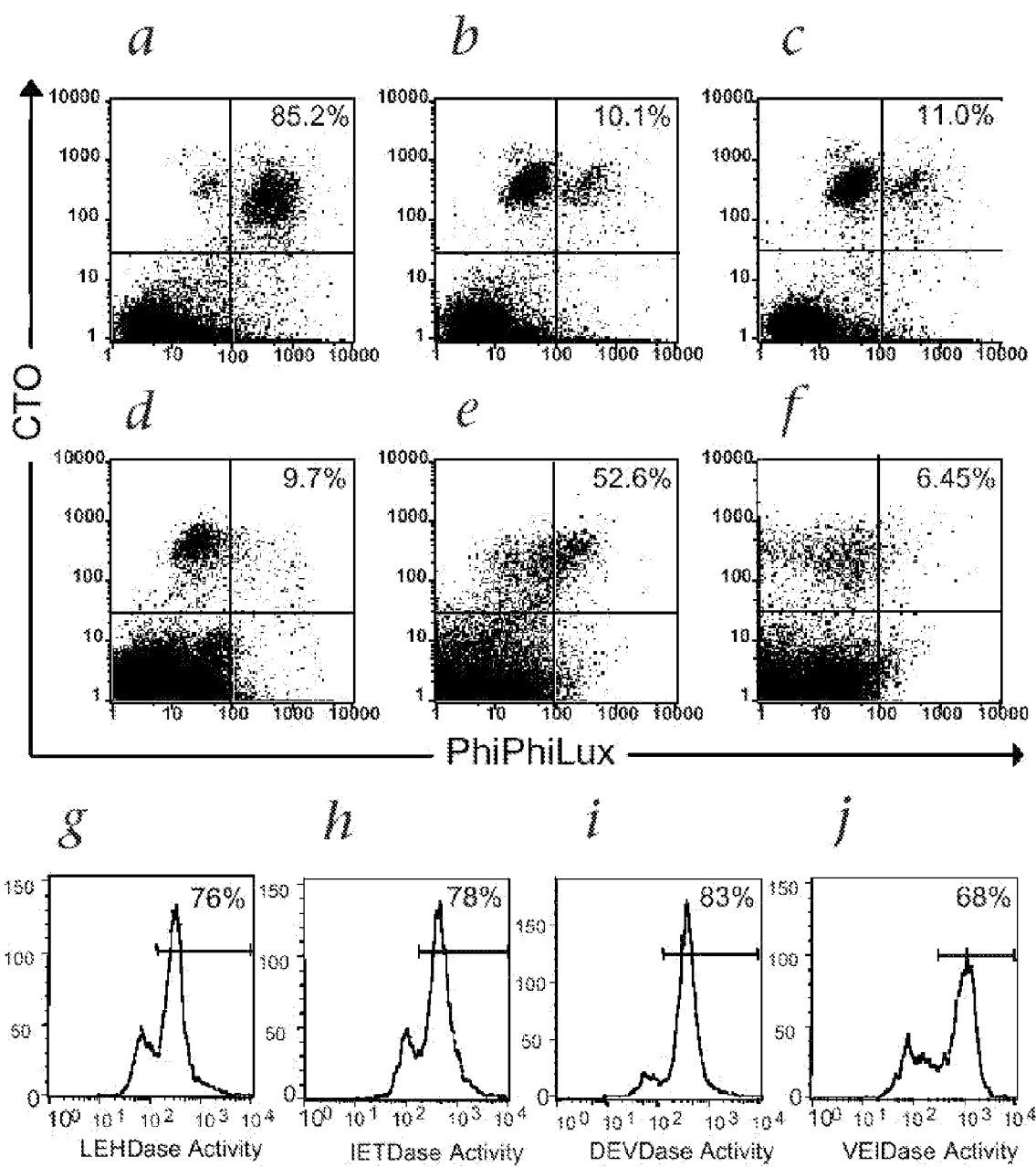
FIG. 1 shows that a fluorescence cellular cytotoxicity (FCC) assay detected strong NP396-404-specific CTL response. Panels a-d, CTO-labeled EL-4 cells were either pulsed with the LCMV peptide NP396-404 (panels a and d), a control polyoma virus peptide MT246-253 (panel b) or no peptide (panel c), and cocultured for 3 h with splenocytes obtained from wild-type (a-c) or perforin-knockout (panel d) C57BL/6 mice 8 d after infection with LCMV. Panels e and f: To test whether virus-infected target cells can be used, CTO-labeled MC57 cells, either infected in vitro with clone 13 strain of LCMV (panel e) or uninfected (panel f) were cocultured with day-8 wild-type B6 effectors. The cell-permeable fluorogenic caspase substrate PhiPhiLux® was added to the cells following the 3-hour incubation. Cells were analyzed by flow cytometry 30 min later. Percentages of caspase+CTO+ target cells in the total CTO+target-cell population are indicated. This experiment is representative of 3-6 similar experiments. Panels g-j: Comparison of different fluorogenic caspase substrates. Four different cell-permeable fluorogenic substrates were used in the fluorescence cellular cytotoxicity (FCC) assay to detect $NP_{396-404}$-specific cell-mediated cytotoxicity in day-8 wild-type B6 effectors. The four substrates measure the following proteolytic activities: LEHDase (caspase-9; panel g), IETDase (caspase-8; panel h), DEVDase (caspase-3; panel i) and VEIDase (caspase-6; panel j). The percentage of apoptotic CTO$^+$ EL4 target cell populations revealed by the different caspase substrates are shown in panels g-j.

A component of the specific host immune response to tumor cells and to intracellular infectious pathogens (including viruses, bacteria and parasites) is the cell-mediated cytotoxicity that results in the killing of cells expressing major histocompatibility complex-associated peptide antigens derived from the pathogen. Cell-mediated cytotoxicity is critical in settings of intracellular infections. During the past three decades many laboratories have studied the role of cell-mediated cytotoxicity mainly with a chromium release assay ($^{51}$Cr assay) that measures the degree of lysis of target cells by cytotoxic T lymphocytes (CTLs) or other effector cells. During recent years alternative techniques have been developed. These are based on the detection of specific cytokines secreted by cytotoxic effector cells after specific activation (Elispot assay, intracellular staining) or by the surface expression of a specific T-cell receptor (tetramers). These techniques measure different properties or function of the antigen-specific T cell activities.

The present invention also pertains to the discovery, using live whole cells and determining the various activated intracellular caspase activities, that cell-mediated cytotoxicity (e.g., a class I restricted a class I-restricted effector cell response directed against a particular antigen) proceeds through the activation of an apoptosis pathway in the target cell (the cell that is killed). Moreover, we discovered that intracellular enzyme activities as well as the order of procaspase activation and the mechanism of procaspase activation found in live whole cells can be different from that observed based on cell free solution enzyme assays or cell free model apoptosis systems. Thus, detection of the activity of an apoptosis pathway (e.g. caspase activity, granzyme A and B, and other cytotoxic cells' granule-derived Granzymes and proteases, nuclear condensation and DNA fragmentation, caspase dependent and independent nucleases, nuclear disruption, etc.) in a target cell contacted with a cytotoxic effector cell (e.g. CTL, NK cell, macrophage, etc.) provides a better measure of class I-restricted cell-mediated cytotoxic activity of the effector cell than that observed with other assays. The assays of this invention are a good replacement for the traditional "chromium release" ($^{51}$Cr) assay.

In general, the assays of this invention involve coincubating and/or contacting a target cell (e.g. an antigen presenting cell (APC)) with a cytotoxic effector cell (e.g. a CTL, an NK cell, a macrophage, etc.); and detecting activity of an apoptosis pathway (e.g. by detecting caspase activity, granzyme activity, nuclear disruption, etc.) in the target cell wherein activity of the apoptosis pathway indicates that the cytotoxic effector cell is active against said target cell.

The assays of this invention find uses in a wide number of contexts. For example, in one embodiment, the assays can be used to screen for the ability of a test agent (e.g. a peptide, a small organic molecule, a vaccine, a nucleic acid, etc.) for the ability to induce a class I-restricted cell-mediated cytotoxicity directed against a particular antigen. This method would involve administering to the subject organism the test agent, obtaining an effector cell from the organism; and measuring cytotoxic activity of the effector cell against a target displaying the antigen, where the cytotoxic activity is measured using the assays of this invention.

Similarly, the assays of this invention can be used to see if a subject has any immunity left from previous vaccinations/immunizations. Known antigens associated with a given vaccine, for example, can be used to detect and quantitate any effector and/or the memory cells present in a given subject's sample cells. For some assay system a given target cell can be infected with a known a virus or a gene or set of genes so that on the membrane surface of the test target cells the desired antigen(s) become displayed, or the test target cells can be pulsed with known antigenic peptides or antigens. Using this assay, the general public can be protected from becoming "over-immunized" and thereby needless exposure of subjects to various vaccine side effects can be avoided. In this context, the test subject provides the effector (memory cells) or the effector cells in the cell-mediated cytotoxicity assay. Known antigens associated with a given vaccine would be displayed on the target cells.

The assays of this invention can be used to evaluate lot to lot consistency in the quality control of vaccine production.

One can also use the assays of this invention to identify the best antigen or combinations of antigens for a particular vaccine (e.g. for a particular year's influenza vaccine).

In another embodiment the assays of this invention are used to determine if a subject has been exposed to (or is presently exposed to) one or more particular antigens.

In still another embodiment the assays of this invention can be used to determine if a subject would reject an heterologous organ or tissue transplant.

As indicated above, the assays of this invention are premised, in part, on the surprising discovery that cell-mediated cytotoxicity proceeds by activation of an apoptosis pathway in the target cell. Thus, any assay that can be used to evaluate activity of an apoptosis pathway can be used to evaluate activity of a cytotoxic effector cell against target cell presenting a particular antigen or combination of antigens.

It was also a surprising discovery that, in particular, caspase activity, is a particularly good marker for cell mediated cytotoxic activity. Thus, in particular embodiments, the activity of one or more caspases in the target cell is detected and provides a measure of the activity of an effector cell (e.g. NK cell, CTL, macrophage) against that target cell.

Methods of detecting apoptosis pathways are well known to those of skill in the art, and numerous kits for apoptosis assays are commercially available. In one approach, the activation of caspases can be assessed by the use of labeled caspase substrates. Thus, for example, FITC or other fluorophores can label caspase substrates at the amino terminal residues or can be conjugated at the P2 residue's amino acid side chain (e.g. such as the lysine residue replacing the valine residue of caspase 3 substrate (DEVD sequence, SEQ ID NO:22)), or replacing the isoleucine residue in the caspase-6 substrate, (VEID, SEQ ID NO:23). This fluorescently labeled peptide substrate can act as a suicide (irreversible) inhibitor or reversible inhibitor of an active caspase. For example a chemically reactive moiety at the P1' position (e.g. fluoromethylketone, chroromethylketone, bromomethylketone and iodomethylketone) can produce a substrate that binds irreversibly to the active caspase. The active caspase, in effect, is covalently labeled by the suicide inhibitor and the label provides a measure of the presence and/or amount of active caspase. Reversible inhibitors can also act similarly. Thus, for example a caspase substrate having an aldehyde moiety in the P1' position, such as FITC-DEVD-CHO (SEQ ID NO:24) can be used similarly.

It will be appreciated that such inhibitors can be produced using other substrates, e.g., granzyme substrates. Thus, for example, using a PD substrate, and/or an IEPD substrate, and/or an IEPDS substrate and/or a VGPDFGR one can provide inhibitors comprising, for example, a reactive moiety (e.g. fluoromethylketone, chroromethylketone, bromomethylketone and iodomethylketone) in the P1' position.

In certain embodiments such inhibitors (e.g., suicide inhibitors) can, optionally, further comprise one or more detectable labels, e.g., (a radio active label, a non-radioactive chromophore, a fluorophore, etc.) on amino terminal residues such as FAM and TMR, Dabcyl, and Edan.

In addition, antibodies (e.g. polyclonal, monoclonal, antibody fragments, single chain antibodies) that specifically bind an active form of a caspase are commercially available (see, e.g., BD PharMingen FITC conjugated monoclonal antibodies, and apoptosis detection kits). In certain embodiments, the antibody specifically recognizes a sequence associated with the newly generated amino terminal residue and/or newly generated carboxyl terminal residue(s) about the procaspase processing site, when the caspase is activated. Also the newly generated procaspase fragments (left over form caspase activation) can be used (detected) to provide a measure of caspase activation. Similarly antibodies can be used to determine the presence of other activive apopotosis-related proteases, granule released proteases (e.g. granule derived proteases such as Granzyme A and B, Cathepsin W, Calpain, and the like).

Antibodies, or other ligands, that specifically recognize the cleavage site of macromolecular targets of caspases (or other apoptosis related protease substrates) can also be useful marker molecules for detecting the presence of active caspases (or other proteases). Other antibodies that specifically recognize the cleavage products of apoptosis-related substrates can be used to assay apoptosis activity as well. The antibodies or ligands can be labeled (e.g. with a fluorophore or chromophores). When the substrate is cleaved, the antibody or ligand will no longer bind and thereby provide a measure of protease activity. Alternatively, antibodies or ligands that specifically bind to the cleavage products of the substrate can be used to provide a direct measure of protease activity. Some examples of macromolecular physiological substrates of caspases include, but are not limited to PARP, nuclear lamin, actin, PKC gamma, SREBP, U1-RNP, DNA-PK, G4-GDI, huntingtin, and HnRNP-C1/2.

In other embodiments, activity of various apoptosis pathway proteases is detected using protease indicators. A wide variety of such indicators are well known to those of skill in the art. Such indicators include any chromophore or fluorophore labeled based protease (e.g. caspase) substrates including, cyclic or linear, mono, dipeptide, tripeptide and tetra peptide to 8, 12, 16, 20, 30, or 31 amino acid residue long peptide substrates having attached one or two chromophores or fluorophores or a combination of chromophores and fluorophores. In certain embodiments, the substrate bears a single chromophore or fluorophore (e.g. at the P1' residue or P2' or P3' up to P8' residue) and typically the amino terminal residues are blocked. However, if the peptide is short then unblocked peptides comprising protease indicators can be also utilized in the present invention. Upon the action of a protease (e.g., a caspase), the newly generated amino terminal residue is no longer blocked. If the chromophore is located at the P1' position, then such cleavage of the bond between the P1 and P1' residue will cause an absorption spectra change and/or the fluorescence intensity change. If this chromophore moiety occupies the P2' or Pn' position, newly generated amino terminal groups will be exposed to intracellularly present amino peptidases or amino dipeptidase activities. Eventually, the peptide bond connecting the chromophore/fluorophore bond is hydrolyzed causing the changes in absorption and/or fluorescence.

Certain indicators include the caspase indicators produced by Marker Gene Technologies. These indicators typically comprise a peptide (protease substrate) where the carboxy and amino terminal of the peptide are both connected to the same fluorophores (e.g. Rhodamine 110) thereby forming a bridge or loop-like structure handing off from the same fluorophores.

Other indicators comprise a protease substrate having a fluorescence resonance energy transfer (FRET) system comprising two fluorophores or a chromophore and a fluorophore with the fluorescence of the latter quenched until the substrate is cleaved by a protease. Certain preferred indicators comprise a homo-double labeled substrate (e.g. a substrate attached to fluorophores of the same species) that form an H-dimer (see, e.g., U.S. Pat. Nos. 5,605,809, 5,714,342, and 6,037,137, and international applications WO9613607 WO 98/37226, and WO/01/18238 and various commercial reagents (e.g. PhiPhiLux® from Oncoimmunin, Inc.). Also contemplated are substrates that form a J-dimer that results in a decrease in fluorescence when the substrate is cleaved.

In certain embodiments, this invention contemplates the use of granzyme B activity indicators for use in the assays described herein. Thus, for example, in certain embodiments this invention contemplates the use of granzyme B activity indicators in target cells as a measure of activity of CTL/NK cells recognition of the target cells and the apoptosis pathway induced by the effector cell's granules derived proteases and/or, in certain embodiments, as a measure of target cell death due to, e.g., NK and/or activities of effector cells. In various embodiments this invention also provides a suicide inhibitor of granzyme B that is attached to a detectable label (e.g. a fluorophore) as well as the use of a specific antibody against granzyme B and/or granzyme A and the detection of these granzymes in the target cells as the measure of CTL and NK activities of the effector cells.

In various embodiments this invention utilizes granzyme B substrates comprising the amino acid sequence VGPDFGR (SEQ ID NO:25) and/or DEVDGIN (SEQ ID NO:26), and/or IEPDS (SEQ ID NO:27), and/or IEPD (SEQ ID NO:28), and/or VGPD (SEQ ID NO:29). In certain embodiments, the granzyme B substrates are suicide inhibitors of granzyme B. In various embodiments the granzyme B substrates/indicators comprise an amino acid sequence selected from the group consisting of KDPC$_5$GIEPDSGC$_5$PKGY (SEQ ID NO:12), C(S-t-Buthio)KDPC$_5$SVGPDFGRGC$_5$PKGY (SEQ ID NO13), GKDPC$_5$SVGPDFGRGC$_5$PKGY (SEQ ID NO:14), DKDPC$_5$SVGPDFGRGC$_5$PKDDG (SEQ ID NO: 15), EDGKDPC$_5$SVGPDFGRGC$_5$PKDDG (SEQ ID NO: 16), KKDPC$_5$SVGPDFGRGC$_5$PKDDG (SEQ ID NO: 17), KKKDPC$_5$SVGPDFGRGC$_5$PKDDG (SEQ ID NO: 18), where C$_5$ is a 6-aminohexanoic acid residue or an episolon-aminocaproic acid residue and C(S-t-Buthio) is a S-t-butylthio-L-Cysteine residue. The substrates/indicators can optionally bear one or more hydrophobic groups (e.g., at the amino terminus) and/or one or more fluorophores and/or chromophores.

In various embodiments the granzyme B activity indicators include, but are not limited to the indicators shown in Table 1.

TABLE 1

Illustrative granzyme B activity indicators.

| Hydrophobic Group | Leader Sequence | Binding Site | Follower Sequence | SEQ ID NO |
|---|---|---|---|---|
| Fa-Fm- | -K-D-P-C$_5$-G- | -I-E-P-D-S | -G-C$_5$-P-K-G-Y- | 12 |
| Fa-Fm- | -C(S-tButhio)-K-D-P-C$_5$- | -S-V-G-P-D-F-G-R- | -G-C$_5$-P-K-G-Y- | 13 |
| Fa-Fm- | -G-K-D-P-C$_5$- | -S-V-G-P-D-F-G-R- | -G-C$_5$-P-K-G-Y- | 14 |
| Fa-Fm- | -D-K-D-P-C$_5$- | -S-V-G-P-D-F-G-R- | -G-C$_5$-P-K-D-D-G- | 15 |
| Fa-Fm- | -E-D-G-K-D-P-C$_5$- | -S-V-G-P-D-F-G-R- | -G-C$_5$-P-K-D-D-G- | 16 |
| Fa-Fm- | -K-K-D-P-C$_5$- | -S-V-G-P-D-F-G-R- | -G-C$_5$-P-K-D-D-G- | 17 |
| Fa-Fm- | -K-K-K-D-P-C$_5$- | -S-V-G-P-D-F-G-R- | -G-C$_5$-P-K-D-D-G- | 18 |

In certain embodiments fluorophores/chromophores are optionally attached to the C terminal lysine residues (underlined K) and/or the N-terminal lysine residues (underlined K) of the sequences shown in Table 1. The fluorophores and/or chromophores can be any one or more of the fluorophores or chromophores described herein. In certain embodiments the fluorophores include, but are not limited to carboxytetramethylrhodamine, carboxyrhodamine-X, carboxyrhodamine 110, diethylaminocoumarin, rhodamine 6G, and carbocyanine dyes. The C4 residue is a 6-aminohexanoic acid residue or an episolon-aminocaproic acid residue. The hydrophobic residues, when present (Fm or Fmoc) or Fa are interchangeable and they are 9-Fluorenylmethoxycarbonyl and 9-Fluoreneactyl groups respectively.

Other approaches to detect activity of an apopotosis pathway include nuclear staining and measurement of nuclear fragmentation, labeling with annexin-V (e.g. annexin-V conjugated with fluorophore (e.g., FITC, TMR, PE and Cy-3, -4, and -5 and -7 dyes) or chromophores staining of target cells) which can readily be adapted for high throughput modalities (e.g. flow cytometry, plate readers, etc.), or confocal microscopy.

While preferred embodiments of the present invention utilize fluorescent or fluorogenic indicators, in certain instances, (e.g. the specific detection of particular components of an apoptosis pathway, particularly where low sensitivity is acceptable) other labels can be used. Such labels include, but are not limited to any composition detectable by spectroscopic, photochemical, biochemical, immunochemical, electrical, optical, electrochromic, or chemical means. Useful labels in the present invention include biotin for staining with labeled streptavidin conjugate, magnetic beads (e.g., Dynabeads™), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Typically, fluorescent or fluorogenic labels are preferred because they provide a very strong signal with low background. They are also optically detectable at high resolution and sensitivity through a rapid scanning procedure.

In certain embodiments, a detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science*, 281: 2013-2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016-2018).

The labels used in the assays described herein can be detected according to any of a wide variety of methods. In certain embodiments, the fluorogenic or fluorescent reagents are detected using, for example a fluorimeter. High throughput screening can be used with, e.g. a cell sorter (e.g. FACS). In certain embodiments, however, methods that permit detecting and/or imaging of single cells are preferred (e.g., using the IN Cell Analyzer of Amersham Bioscience, Opera of Evotec Technologies, and ImageStream cell analysis systems of Amnis Corp.). Such methods are well known to those of skill in the art and include, but are not limited to fluorescence microscopy, cell analyzers, and the like. It was a surprising discovery of this invention that show surprisingly high sensitivity in detecting the memory cells' cytotoxicity activity as compared with the conventional radioactive chromium 51 release assay.

In certain embodiments, the detection methods involve measuring fluorescence intensity and/or anisotropy, and/or fluorescence lifetime using, for example BlueShift™, or Evotec (Opera™) devices.

In certain embodiments, the assays are run in various standard culture containers including, but not limited to plastic or glass tubes or culture vessels, multi-well plates, and the like.

In certain embodiments, the assays can be performed in microfluidic channels. The detection of signal can then be accomplished by either confocal images of cells passing through the optically acceptable microfluidic channel window or simple fluorescence imaging of cells. The observed fluorescence single images are captured and the corresponding single cell images are analyzed for intracellular fluorescence intensity level determination. The size of the microfluidic channel can determine the detection scheme. For example, if the channel is less than about 200 µm, a simple fluorescence image of the target cell samples can be utilized under multiple wavelengths. Thus, for example, three wavelengths can be utilized, e.g., one UV and two visible (e.g. green (488 nm) and red (greater than 560 nm)).

Using microscopic cell image analysis software such as Image-Pro Plus (Media Cybernetics, Silver Spring, Md.) one can quantitate and carry out a cellular population analysis where the desired target cells are identified and the cell number counted by UV excitation of cell permeable labels (e.g. a cell permeable nuclear staining Heachst dye). Similar flow cytometry population histograms or sample analyses can be performed.

Certain embodiments utilize two microfluidic channels arranged side by side where the channel wall separating the two channels consists of a membrane that is porous and that allows passage of a particle of, e.g., size 10 µm or less. Such a porous wall allow free crossing of virus particles and bacteria and other pathogens. Culture media in this channel without the cells can be exposed to air samples by bubbling through the media reservoir and the pathogens are collected and concentrated. This fluid is then passed through the channel where the effector and target cell samples are located across such porous channel wall in the adjacent microfluidic channel.

EXAMPLES

The following examples are offered to illustrate, but not to limit the claimed invention.

Example 1

Visualization and Quantification of T Cell-Mediated Cytotoxicity Using Cell-Permeable Fluorogenic Caspase Substrates Following T-cell receptor recognition of antigenic peptide-MHC class I complexes on the surface of target cells, cytotoxic effector cells (e.g., CTLs) induce target-cell apoptosis either through directed exocytosis of perforin and granzymes or through ligation of "death receptors" in the Fas/Fas ligand (FasL) pathway. An immediate event following both types of cytotoxic signaling is the activation of the caspase cascade within the target cells (Atkinson et al. (1998) *J. Biol. Chem.* 273: 21261-21266). We have used a novel class of cell-permeable fluorogenic caspase substrates to develop a fluorescence-based cellular cytotoxicity (FCC) assay that detects CTL-induced caspase activation within individual target cells (Packard et al. (1996) *Proc. Natl. Acad. Sci. USA* 93: 11640-11645; Komoriya et al. (2000) *J. Exp. Med.* 191: 1819-1828). These reagents are composed of two fluorophores covalently linked to 18-amino-acid peptides containing the proteolytic cleavage sites for individual caspases. In the uncleaved substrates, fluorescence is quenched due to the formation of intramolecular excitonic dimers. Upon cleavage of the peptides by specific caspases, the fluorophore-fluorophore interaction is abolished, leading to an increase in fluorescence that can be detected by a variety of methods including, but not limited to flow cytometry or fluorescence microscopy. Given that caspase activation in target cells occurs shortly after the CTL-target-cell encounter, detection of caspase activation within intact target cells provides an early and biologically relevant measurement of CTL-mediated apoptosis.

Quantification of CTL Activity Using the Fluorescence Cellular Cytotoxicity (FCC) Assay.

We have used the murine lymphocytic choriomeningitis virus (LCMV) infection as the model system to develop the fluorescence cellular cytotoxicity (FCC) assay. Infection of C57BL/6 mice with the Armstrong strain of LCMV elicits a vigorous CTL response against a defined array of MHC class I-restricted viral epitopes and the frequencies of antigen-specific $CD8_+$ T cells peak eight days after infection (Murali-Krishna et al (1988) *Immunity* 8: 177-187). We first used the DEVDase (caspase-3/7) substrate, PhiPhiLux®, to measure the CTL response against the immunodominant nuclear protein epitope $(NP)_{396\text{-}404}$ by multiparameter flow cytometry. Target EL4 ($H-2_b$) cells were labeled with the fluorescent probe CellTracker Orange (CTO) and pulsed with $NP_{396\text{-}404}$, an irrelevant control polyoma virus peptide middle T protein epitope ($MT_{246\text{-}256}$), or no peptide. CTO labeling permits distinction of target cells from effector cells. Target cells were then co-incubated with fresh splenocytes obtained directly from mice 8 days following LCMV infection at an effector-totarget (E:T) ratio of 50:1 for 3 hours. Following this incubation, cells were labeled with PhiPhiLux® to detect intracellular DEVDase activities. As shown in FIG. 1, panel a, 85.2% of the target cells ($CTO^+$) pulsed with peptide $NP_{396\text{-}404}$ were positive for DEVDase activity, whereas the background DEVDase activity of EL4 cells pulsed with the control peptide (FIG. 1 panel b) or no peptide (FIG. 1, panel c) was around 10%. The DEVDase activities were assessed by using caspase 3/7 substrate a containing caspase 3/7 recognition tetra peptide amino acid sequence of apspartyl-glutanyl-valyl-aspartyl (SEQ ID NO:30). This substrate, available from OncoImmunin, Inc. as PhiPhiLux®™ and comprising the sequence $KDPC_5GDEVDGIDC_5GPKGY$ (SEQ ID NO:31) is described in U.S. Pat. No. 6,037,137, which is herein incorporated by reference in its entirety). The specific detection of CTL-induced target-cell apoptosis was further confirmed by the inability of effector cells obtained from LCMV-infected perforin-knockout mice to mediate cell killing as assessed by this assay (FIG. 1, panel d).

Observed Caspase Activation in the Target Cells are Mediated by the Granule Derived Protease Released and Introduced to the Target Cell Via Pore Forming Perform.

The specific detection of CTL-induced target cell apoptosis was further confirmed by the inability of effector cells obtained from LCMV-infected perforin-knockout mice to mediate cell killing as assessed by this assay (FIG. 1, panel d). As the name indicate, perforin-knockout mice would not have any cytotoxic cells with the pore forming protein, thus such cells are not capable of "injecting" into the target cells granule derived proteases such as Granzyme B. The panel d shows only 9.7% of apoptotic cells which is the same level of dead cells as found in the panel b with negative control peptide or in the panel c, where no peptide was added. This background death or default death level of about 9 to 10% is to be compared with the death figure for the positive cytotoxic sample in the panel a and the observed death was over 85%.

Fluorescence Based Cellular Cytotoxicity (FCC)) Assay can Detect the Target Cells Actively Infected with Virus.

We also measured the total CTL activity against cells actively infected with LCMV using the fluorescence cellular cytotoxicity (FCC) assay. For this analysis, MC57 fibroblasts were infected in culture with LCMV clone 13 and used as target cells. Strong LCMV-specific CTL activity was detected as 52.6% of the infected target cells were killed, whereas the background apoptosis was 6.45% of the uninfected target cells (FIG. 1, panels e and f).

Fluorescence Based Cellular Cytotoxicity (FCC) Assay can Detect the Target Cells Actively Infected with Virus.

Fluorogenic substrates containing recognition and cleavage sequences for alternative caspases also detected significant target-cell death induced by the strong $NP_{396-404}$-specific CTL activity. This $NP_{396-404}$ is known to be a strong antigenic epitope for the LCMV antigen. The amino-acid sequences included in these substrates contain reported cleavage sequences for caspase-9 (LEHDase), caspase-8 (IETDase), or caspase-6 (VEIDase) (Thornberry et al. (1997) *J. Biol. Chem.* 272: 17907-17911) All four reagents detected a significant target-cell death induced by the strong $NP_{396-404}$ specific CTL activity (FIG. 1, panels g-j), with the levels of caspase activities in EL4 cells pulsed with the control peptide consistently lower than 15% (data not shown). Notably, labeling with the VEIDase substrate gave the brightest positive signals, whereas the percentage of VEIDase, cells was somewhat lower than those seen following labeling with other caspase substrates. The relative brightness of the signals is consistent with our earlier studies in which we measured the relative abundance of different activated caspases present at specific times after induction of apoptosis (Komoriya et al. (2000) *J. Exp. Med.* 191: 1819-1828). Furthermore, as caspase-6 is downstream of caspase-8 and -9 and in some cases caspase-3 in the caspase activation cascade, it might be expected that more caspase-positive cells will be revealed using substrates that are cleaved earlier in the process of programmed cell death when a three-hour assay is employed (Id.). More prolonged effector and target-cell incubation before caspase substrate exposure should result in similar levels of signal from different caspase substrates, and we found no significant difference between fluorescence signals from VEIDase and DEVDase substrates following a 20 hour incubation of effectors and targets (data not shown).

Figure 2:
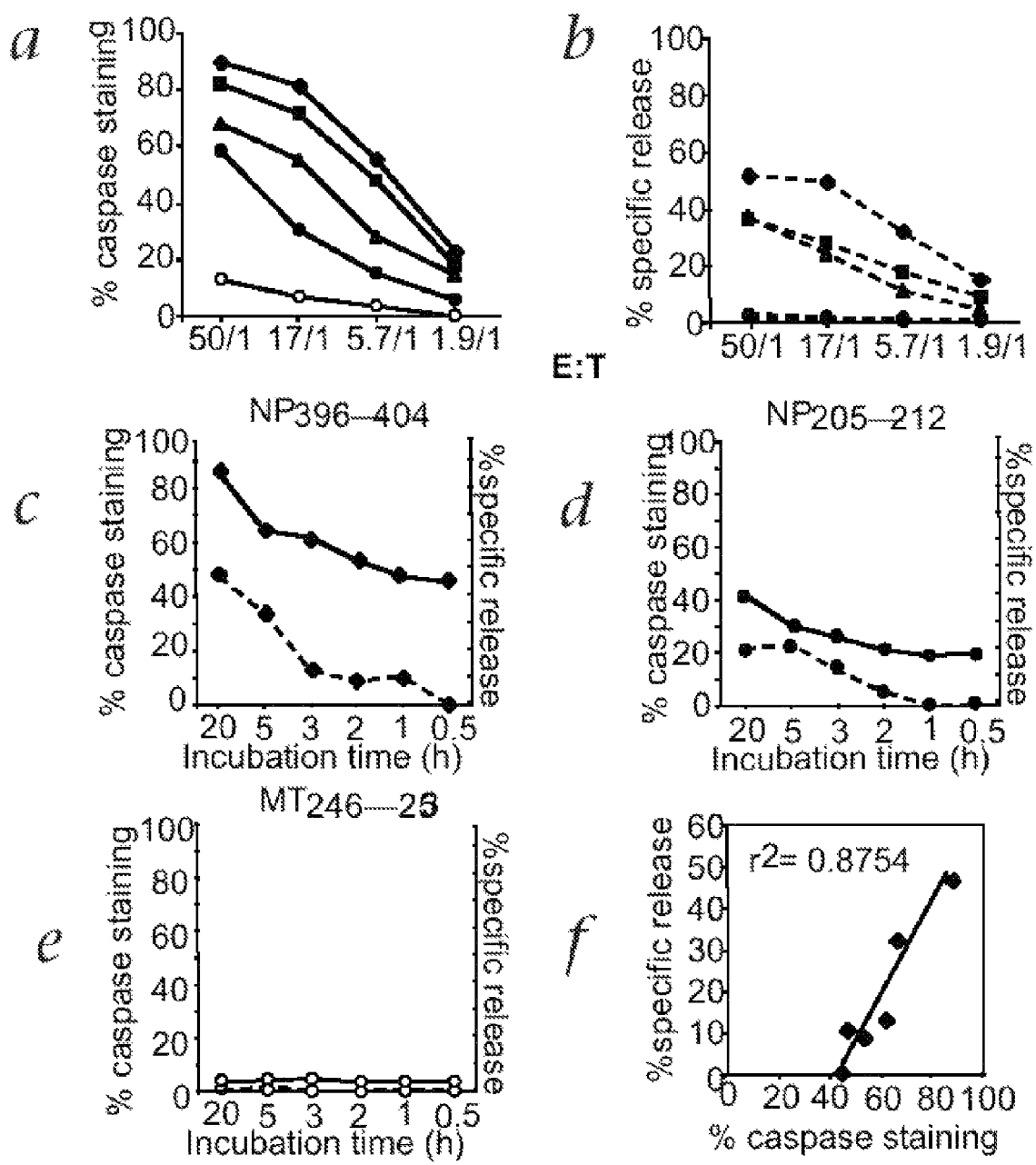
FIG. 2 shows a comparison of CTL activities specific for a panel of LCMV epitopes measured by fluorescence cellular cytotoxicity (FCC) and $^{51}$Cr-release assays. CTO or $^{51}$Cr-labeled EL4 cells were pulsed with LCMV peptides $NP_{396-404}$ (♦), $GP_{33-42}$ (■), $GP_{276-286}$ (▲), $NP_{205-212}$ (●) or polyoma virus peptide MT246-253 (○) and then cocultured with splenocytes obtained from a C57BL/6 mouse 8 d after LCMV infection. The CTL-mediated killing of the target cells were then assessed by either the fluorescence cellular cytotoxicity (FCC) assay using PhiPhiLux® (solid line) or the $^{51}$Cr-release assay (dashed line). Panels a and b, Effectors and targets were incubated at various E:T ratios for 3 h (fluorescence cellular cytotoxicity (FCC) assay) or 5 h (51Cr-release assay). Panels f: A linear regression analysis was performed on the data of panel c, Effectors and targets were incubated at an E:T ratio of 25:1 for indicated lengths of time. A linear regression analysis was performed on the data presented in panels c-f. Data represent 2 independent experiments.

Comparison of the Fluorescence Cellular Cytotoxicity (FCC) Assay with the $^{51}$Cr-Release Assay To directly compare the fluorescence cellular cytotoxicity (FCC) assay with the $^{51}$Cr-release assay, we measured CTL activities against a panel of LCMV peptides using the two methods in parallel. Day 8 splenocytes were incubated with EL4 target cells pulsed with different peptides at various E:T ratios for 3 hours (FCC assay) or 5 hours ($^{51}$Cr-release assay). The two methods detected an identical pattern of dominance hierarchy of the CTL activities specific for different peptides (FIG. 2, panels a and b). The FCC assay was more sensitive than the $^{51}$Cr-release assay in detecting the CTL response specific for the subdominant epitope $NP_{205-212}$ (FIG. 2, panel a).

To further test the reliability of the fluorescence cellular cytotoxicity (FCC) assay, we performed a kinetic comparison of CTL activities measured by both the FCC and $^{51}$Cr-release assays. $NP_{396-404}$, $NP_{205-212}$ and $MT_{246-253}$ were used to pulse target EL4 cells (FIG. 2, panels c-e). Effector splenocytes were incubated with EL4 cells at an E:T ratio of 25:1 for various lengths of time from 30 minutes to 20 hours. At all time points, the FCC assay detected a higher percentage of target-cell killing induced by CTLs specific for both LCMV epitopes than that of the $^{51}$Cr release assay. A linear regression analysis of the two sets of data in FIG. 2, panel c, revealed a strong positive correlation ($r^2$=0.8754) between the percent caspase target cells and the percent specific $^{51}$Cr release (FIG. 2, panel f). Differences between the specific killing measured by the two assays are more pronounced at the earlier time points (FIG. 2, panels c and f). This is consistent with the fact that the FCC assay detects caspase activation, which is one of the earliest events in CTL-mediated apoptosis, whereas the $^{51}$Cr-release assay detects cell lysis, a much later occurring event in cell death. Taken together, these results demonstrate that compared with the conventional $^{51}$Cr-release assay, the FCC assay provides a more sensitive and rapid method to detect antigen-specific CTL responses.

Figure 3:
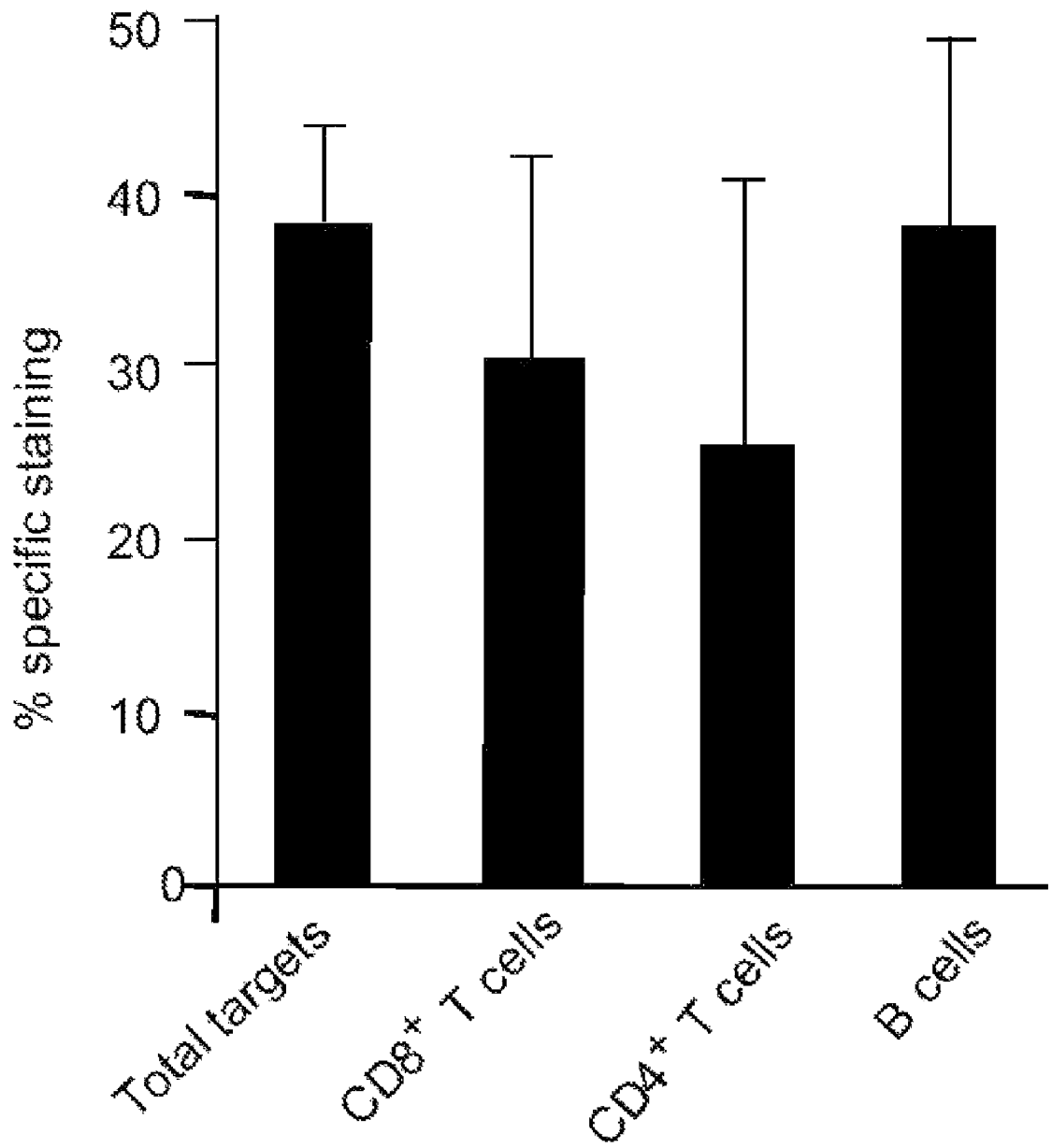
FIG. 3 illustrates LCMV-specific CTL killing of primary target cells detected by a fluorescence cellular cytotoxicity (FCC) assay. CTO-labeled naive splenocytes were pulsed with either $NP_{396-404}$ or $MT_{246-253}$ and then cocultured with splenocytes from a C57BL/6 mouse 8 d after LCMV infection. After addition of PhiPhiLux® and a 30-min incubation, cells stained with monoclonal antibodies against CD3, CD8 and B220. The percentage of PhiPhiLux® cells in each cell subset was calculated, and percent specific staining in each subset was calculated as: % caspase staining of $NP_{396-404}$-pulsed cells—% caspase staining of $MT_{246-253}$-pulsed cells. Data represent the average of 4 independent experiments (mean±s.d.).

Fluorescence Cellular Cytotoxicity (FCC) Assay Detects CTL Killing of Primary Target Cells Primary cells, in contrast to immortalized cells lines, take up $^{51}$Cr poorly and are therefore not commonly used in CTL assays. As a result, the range of cell types that may be effectively killed by CTLs in vivo remains largely unknown. However, this question is key in understanding certain cancers and chronic infections where transformed or infected cells are able to evade immune clearance and persist in the host. To test whether primary cells can be used as suitable target cells in the fluorescence cellular cytotoxicity (FCC) assay, we labeled naive splenocytes with CTO, pulsed them with specific peptides, and then cultured them with day 8 effector splenocytes at an E:T ratio of 25:1 for 3 hours. Following PhiPhiLux® labeling, fluorophore-conjugated monoclonal antibodies against CD4, CD8 and B220 were used to label different subsets of target cells. By gating on different target-cell subsets, the percentages of apoptotic cells in $CD4^+$ T-cell, $CD8^+$ T-cell and $B220^+$ B-cell populations were calculated. All three subsets of primary lymphocytes were induced to undergo apoptosis when pulsed with the $NP_{396-404}$ peptide, with B cells showing slightly higher susceptibility to CTL killing (FIG. 3). The greater susceptibility of B cells to CTL-mediated killing is consistent with their expression of higher levels of both MHC class I and costimulatory molecules than T cells. These results demonstrate the unique ability of the FCC assay to study the susceptibility to CTL killing of various primary target-cell subsets.

Direct Visualization of the CTL Killing Process

Figure 4:
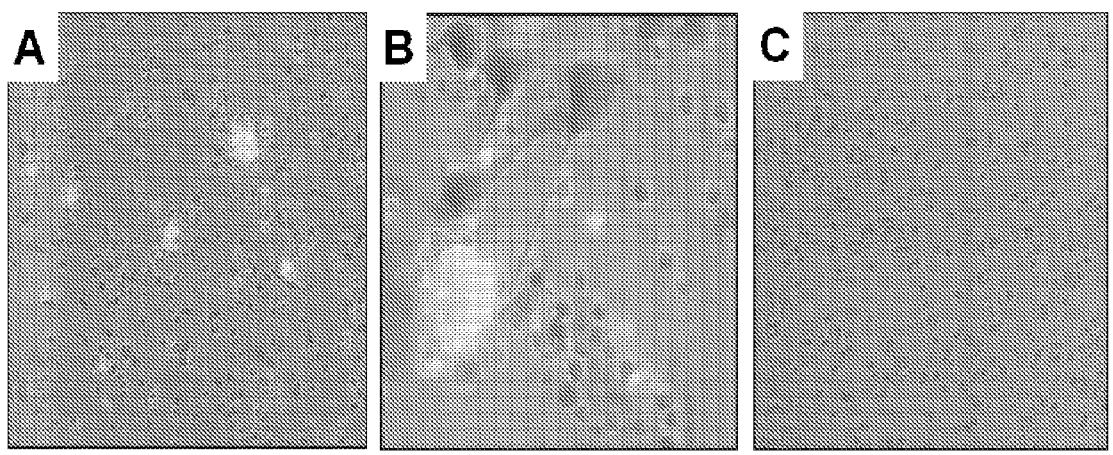
FIG. 4 shows cell-mediated killing of target cells directly visualized using fluorescence microscopy. Panels a-c, MC57 target cells, when pulsed with $NP_{396-404}$ (panels a and b) but not $MT_{246-252}$ (panel c), were recognized and attached by spleen cells from a C57BL/6 mouse 8d following LCMV infection (small round cells) and induced to undergo apoptosis as detected by PhiPhiLux® cleavage. Magnifications: ×40 (panels a and c); ×200 (panel b).

To directly visualize the CTL killing process, we also investigated the ability of fluorescence microscopy to reveal the activation of caspases in target cells. Target cells pulsed with specific or control peptides were admixed with day 8 splenocytes from LCMV-infected mice. MC57 cells pulsed with the $NP_{396-404}$ were recognized by effector cells and induced to undergo apoptosis (FIG. 4, panels a and b). In contrast, pulsing with the control peptide, $MT_{246-253}$ did not result in caspase activation in target cells (FIG. 4, panel c). Thus, cellular contact between effectors and targets and the subsequent CTL-induced caspase activation in target cells were directly visualized by fluorescence microscopy. Interestingly, although effector cells induce apoptosis in target cells following cell-to-cell contact, they themselves did not seem to undergo apoptosis at that moment, as revealed by their lack of cleavage of the PhiPhiLux® caspase substrate (FIG. 4, panel b). Through the simultaneous use of the fluorescence cellular cytotoxicity (FCC) assay and epitope-specific MHC tetramer staining, we are currently investigating the fate of effector cells in real time during and after the killing process—an issue that cannot be addressed using the $^{51}$Cr-release assay due to the inherent obscurity of the cell-culture milieu used in this traditional method.

In summary, we have developed a novel non-radioactive, fluorescence-based cytotoxicity assay to detect antigen-specific CTL function. Unlike conventional $^{51}$Cr-release assays, the fluorescence cellular cytotoxicity (FCC) assay enables monitoring of cellular immune responses in real time and at the single-cell level using diverse fluorescence detection methods such as flow cytometry, as well as fluorescence and confocal microscopy. This assay can be used to study CTL-mediated killing of primary host target cells, and enables assessment of important biological details of the killing process, as well as the fate of immune effector cells during the killing process. It can also better detect relatively weak CTL response against subdominant epitopes or low levels of direct ex vivo memory CTL responses. These features should enable direct determination of whether specific sub-populations of cells can resist CTL-mediated lysis (for example, tumor cells or certain virus-infected cells) (Ploegh (1998) *Science* 280: 248-253) or, alternatively, induce apoptotic deletion of the CTL effectors themselves (for example, through expression of FasL on specific tumors or immunologically privileged tissues, or as an immune evasion strategy employed by immunodeficiency viruses) (Collins et al. (1998) *Nature* 391: 397-401). Although using the murine LCMV infection model as the primary model, we have demonstrated that this novel approach is also readily applicable to study host cellular immune responses in other infection models including, but not limited to, human immunodeficiency virus, simian immunodeficiency virus, cytomegalovirus and Epstein-Barr virus, and the like. In addition, the assay can be easily utilize human adherent and suspension cells as target cells when one uses human NK cells as the effector cells. We demonstrated that one can substitute the caspase 3/7 substrate, DEVDase substrate with the caspasae 6 substrate containing the tetrapeptide, VEID, caspase protease indicator(s). We have also demonstrated that other caspase activity indicator molecule(s) can be replaced with cell permeable fluorogenic caspase substrate(s) that allow the direct measurement of intracellular caspase activities. Because the fluorescence cellular cytotoxicity (FCC) assay is readily adaptable to quantitative fluorescent scanning platforms, it also provides a high throughput method to quantitate CTL activity with broad applicability to basic and applied studies of the cellular immune response. The favorable attributes of the FCC assay permits new insights into research questions concerning the pathogenesis of infectious, malignant and immunological diseases that have been experimentally unapproachable previously, and provides a practical and useful method to quantify CTL activity in basic and applied studies of the cellular immune response.

Methods

Mice and Virus Infection.

6-8-wk-old female wild-type C57BL/6 mice (H2-$_b$) were purchased from the Jackson Laboratories (Bar Harbor, Me.). Mice were infected with 2×10$^5$ plaque-forming units (p.f.u.) of LCMV Armstrong strain (provided by R. Ahmed) intraperitoneally (i.p.) and spleens were collected at day 8 postinfection. Infection of MC57 cells with the clone 13 strain of LCMV was carried out at a MOI=2 for 48 h at 37° C. All animal studies were approved by the institutional Animal Care And Use Committee of Emory University.

Synthetic Peptides.

LCMV peptides NP$_{396-404}$ (FQPQNGQFI, SEQ ID NO:32), GP$_{33-41}$ (KAVYNFATC, SEQ ID NO:33), GP$_{276-286}$ (SGVENPGGYCL, SEQ ID NO:34), NP$_{205-212}$ (YTVKYPNL, SEQ ID NO:35) and polyoma virus peptide MT$_{246-253}$ (SNPTYSVM, SEQ ID NO:36) were synthesized as described (Ruppert et al (1993) *Cell* 74: 929-937). Stock solutions (40 mg/ml) were prepared in dimethyl sulfoxide (DMSO).

Flow-Cytometry Fluorescence Cellular Cytotoxicity (FCC) Assay

Target cells were suspended in complete RPMI1640 medium containing 10% heat-inactivated FBS at 1×10$^6$ per ml in 6-ml polypropylene tubes (Becton Dickinson Labware, Lincoln, N.J.). Cells were incubated in a 37° C., 5% CO$_2$ incubator for 1 h in the presence of 3 μM CTO (Molecular Probes, Eugene, Oreg.) and viral peptides (1 μg/ml). The cells were then washed once and resuspended in complete medium at 1×10$^6$/ml. Single effector cell suspensions were prepared at various concentrations depending on the E:T ratios. Target-cell suspension (100 μl) was cultured with effector cells (100 μl) in each well of a 96-well, round-bottom plate at the various E:T ratios for various length of time at 37° C. as indicated in the text and figure legends. The supernatant was then removed and the cells were incubated in 75 μl per well of the indicated caspase substrate (10 μM, OncoImmunin, Gaithersburg, Md.) for 30 min at 37° C. followed by two washes with PBS. If immunophenotypic analysis was needed, the cells were incubated with 100 μl/well of the monoclonal antibody dilutions on ice for 20 min followed by two washes with cold PBS. The following monoclonal antibodies were used: PerCP-anti-CD3ε (145-2C11), APC-anti-CD8α (Ly-2), APCanti-CD45R/B220 (RA3-6B2). All monoclonal antibodies were purchased from BD PharMingen (San Diego, Calif.).

Flow Cytometry and FACS Analysis.

Following the fluorescence cellular cytotoxicity (FCC) assay, cells were resuspended in 250 μl PBS per well and samples were acquired using a FACSCalibur flow cytometer (Becton Dickinson, San Jose, Calif.). The cleaved caspase substrate has the following fluorescence peak characteristics: $\lambda_{ex}$=505 nm and $\lambda_{em}$=530 nm, and and is detected in the FL1 channel. CTO is detected. The data were analyzed using FlowJo software (Tree Star, San Carlos, Calif.). Unless specified in the text, the percentage of caspase-positive cells in target-cell population was calculated as: % caspase staining= [(caspase$^+$CTO$^+$cells)|(caspase$^+$CTO$^+$+caspase$^-$CTO$^+$)]× 100%.

Fluorescence Microscopic FCC Assay.

MC57 (H-2$_b$) cells were adhered to the bottom of a 24-well tissue culture plate at 1×10$^5$/well for 4 h. Effector cells were added into the wells (2.5×10$^6$ 200 μl of RPMI1640 medium with 10% fetal bovine serum) and the plate was incubated at 37° C. for 3 h. PhiPhiLux® (75 μl/well) was then added after carefully removing the supernatant. Following a 30-min incubation at 37° C., the plate was examined using a Nikon Eclipse TE300 fluorescence microscope (Nikon, Tokyo, Japan) and the image was captured by a SPOT digital camera model SP401-115 (Diagnostic Instruments, Sterling Heights, Mich.).

$^{51}$Cr-Release Assay.

$^{51}$Cr-release assays were performed as described (Liu et al. (1999) *J. Virol.* 73: 9849-9857). CTL activity was calculated as the percentage of specific $^{51}$Cr release using the following equation: % specific killing=(sample release−spontaneous release)/(maximal release−spontaneous release)×100%.

Example 2

Cell Permeable Fluorogenic Caspase Substrates Show the Presence of Memory Cells where as the Tradition Chromium Release Assay Did not Detection of memory CTL responses using chromium release assay generally requires a 5 to 6-day in vitro restimulation and the expansion of CTL precursors in culture. With the improved sensitivity of fluorescence cellular cytotoxicity (FCC) assays described herein, we believed that we would be able to detect a memory CTL response with limited or no in vitro restimulation.

Figure 5:
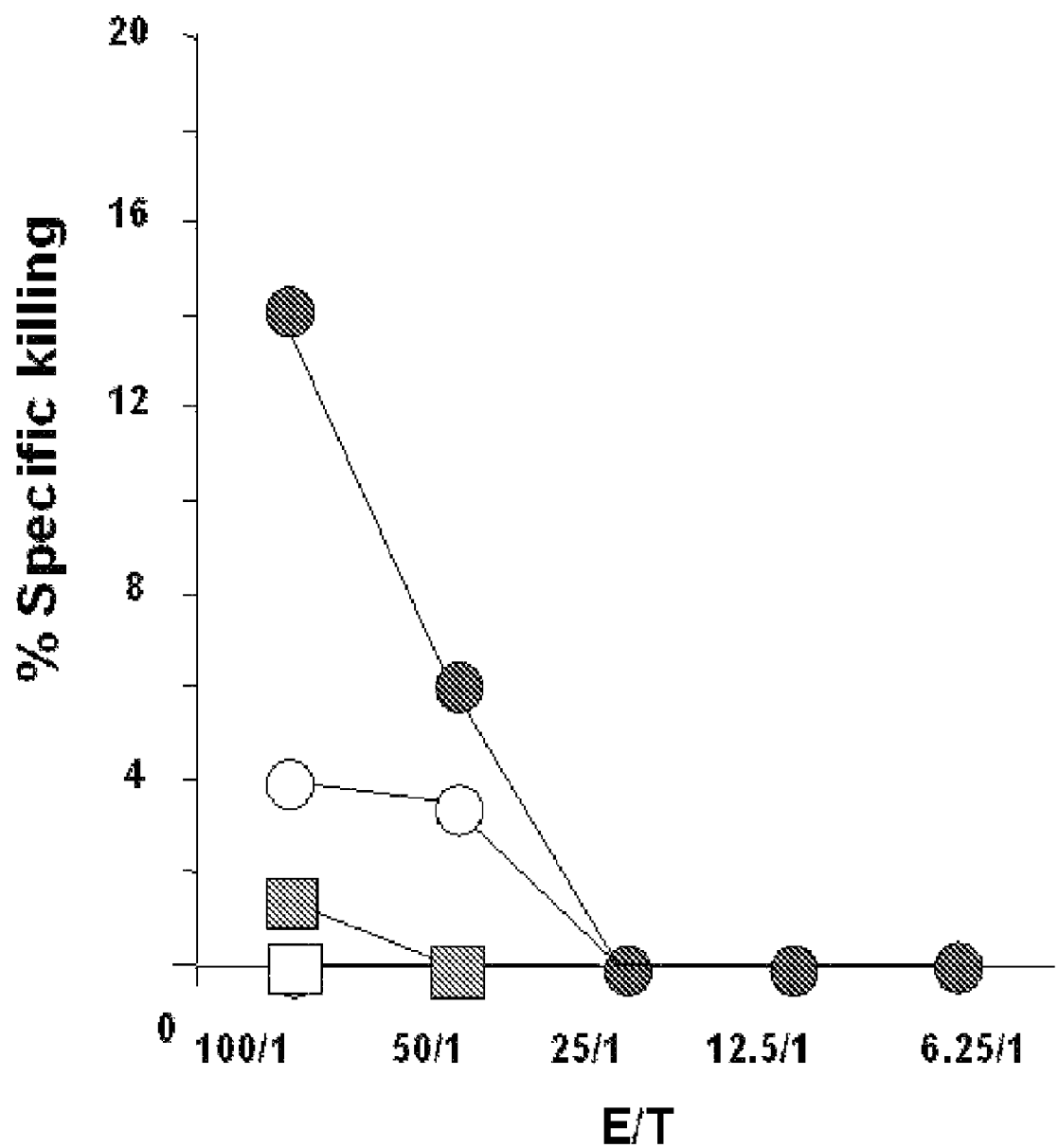
FIG. 5 shows that a fluorescence cellular cytotoxicity (FCC) assay better detected direct ex vivo memory cell-mediated cytotoxicity against NP396-404 peptide. EL-4 cells were labeled with CTO, pulsed with either NP396-404 (solid circles and squares) or MT246-254 (hollow circles and squares) and then incubated with spleen cells from C57BL/6 mice 32 days following LCMV infection. This was followed by measurement of caspase-3 activity (circles) or chromium release (squares). These data are representative of three similar experiments.

To test this hypothesis, direct ex vivo memory CTL activity specific for $NP_{396-404}$ was measured using both the fluorescence cellular cytotoxicity (FCC) and $^{51}$chromium release assays. Freshly prepared spleen cells obtained from LCMV-infected C57BL/6 mice 32 days after initial LCMV infection were incubated at various E/T ratios with target EL4 cells for 5 hours. FIG. 5 shows that, surprisingly, the fluorescence cellular cytotoxicity (FCC) assay but not $^{51}$chromium release assay detected $NP_{396-401}$-specific memory CTL activity at E/T ratios higher than 25/1. However, as expected, the direct ex vivo memory CTL response is much weaker comparing to the CTL response during the effector phase of the immune response (FIGS. 2 and 5). Restimulation conditions can be optimized to can fully activate the lytic potential of memory $CD8^+$ T cells within a minimum length of in vitro culture time. The ability of various co-stimulatory signals to activate memory T cells in fluorescence cellular cytotoxicity (FCC) assay will be evaluated, as they have been employed in intracellular cytokine assay to enhance $CD4^+$ T cell functions.

Example 3

Cellular Cytotoxicity Assay Using Various Adherent and Suspension Cells as the Target Cells In order to evaluate the broader applicability of the present invention, we have tested assay performance using both an adherent cells as well as additional suspension cells as the target cells. The effector cells in this experiment were human NK cells. The percentage killing (see Table 2) observed for just 1 hour of co-incubation of the effector cells with an effector to target cell ratio of 5 to 1 shows clearly that the cell-mediated cytotoxicity described herein works very well with these widely different cell types, i.e. the adherent human breast adenocarcinoma cell and human suspension cells (Jurkat and K562).

An alternative assay was also performed where the VEI-Dase substrate (VEID, SEQ ID NO:23) rather than DEVDase substrate (DEVD, SEQ ID NO:22) was used. It has been reported that this caspase 6 substrate with the VEID tetrapeptide amino acid sequence is also recognized by cytotoxic cells' granule-derived protease, granzyme B.

TABLE 2

Cellular cytotoxicity assay using various cell types (adherent and suspension cells). MDA-MB-468 = adherent human breast adenocarcinoma cells. Jurkat = non-adherent human acute T-cell leukemic cells. K562 = human chronic myelogenous leukemic cells. NK-92 = human NK cells.

| Effector Cells | Target Cells Adherent Cells | Target Cells Nonadherent Cells | E:T Ratio | Co-Incubation Time (Hr) | % Killing |
|---|---|---|---|---|---|
| NK-92 |  | Jurkat | 5 to 1 | 1 | 74% |
| NK-92 |  | K-562 | 5 to 1 | 1 | 34% |
| NK-92 | MDA-MB-468 |  | 5 to 1 | 2.5 | 48% |

Example 4

Cellular Cytotoxicity Assays Using Various Apoptosis/Caspase Activity Marker and Protease Indicators Although certain preferred embodiments of this invention utilize cell permeable fluorogenic protease indicator molecules such as the DEVDase and VEIDase substrates of OncoImmunin, Inc. (see, e.g., U.S. Pat. No. 6,037,137) other potential caspase protease indicator molecules were evaluated for use in the methods described herein.

One indicator was a fluorogenic suicide substrate and another indicator was bis-(Z-DEVD amide)-rhodamine 110. These indicators were used along with CaspaLux®6-J1D2 (VEID substrate) as a reference. The same target, Jurkat cells and the same E:T ratio of 5 to 1 were used. The effector and target cell co-incubation time was 1 hour and to show that the preferred protease indicator (VEIDase substrate) is sensitive and the assay response time can be as short as 1 hour, two hour time points are also presented (see Table 2).

The results derived using the bis-(Z-DEVDamide)-Rhodamine 110 are markedly lower than the other two protease indicators. The phycoerythine (PE) labeled annexin V as a marker of apoptosis or a marker of cells with active caspases was used to evaluate the performance level. Although Annexin V binding to the cell surface of the apoptotic cells due to the appearance of phosphotadylserine from the inner leaflet of the plasma membrane to outer leaflet is an indirect reflection of the presence of active caspases, the % killing observed was similar to other class of caspase protease indicator molecule Fluorescein-VAD-fmk, 65.5% and 63.2% respectively.

The latter protease indicator molecule tags those procaspases that are activated binding to the active site of caspases irreversibly. The reactive functional group fmk can potentially cross-react with other cellular macromolecules. Hence, it is an indirect protease indicator although often used in practice as a specific caspase probe. For the experiment using PE-annexin V, the indicator molecule is red with cell tracker green (Molecular Probes Inc.) used to label all target cells rather than the cell tracker orange as used the examples above.

TABLE 3

Cellular cytotoxicity assay using various apoptosis/caspase activity marker and protease indicators. PE is phycoerythrin. FMK is fluoromethylketone. VAD = 1 letter code tripeptide amino acid sequence or l-valyl-l-alanyl-l-aspartyl (SEQ ID NO:37). CaspaLux ®6-J1D2 = VEIDase substrate. Bis-(N-CBZ-DEVD amide)R22120 = Bis-(N-CBZ-aspartyl-glutamyl-valyl-aspartylamide)Rhodamine 110

|  | Effector and Target Cell Ratio Used | Cellular Co-Incubation Time (hr) | % Killing |
|---|---|---|---|
| Cell Surface Marker |  |  |  |
| PE-labeled Annexin V | 5 to 1 | 1 | 65.6% |
| Intracellular Caspase Activity Markers |  |  |  |
| Indirect Activity Indicator |  |  |  |
| Fluorescein-VAD-fmk | 5 to 1 | 1 | 63.2% |
|  | 5 to 1 | 2 | 68.2% |
| Direct Activity Indicator |  |  |  |
| CaspaLux ®6-J1D2 | 5 to 1 | 1 | 75.0% |
| Bis-(N-CBZ-DEVD amide)R22120 | 5 to 1 | 1 | 48%% |
|  | 5 to 1 | 2 | 75.4% |

Example 5

A Single Cell-Based Fluorogenic Cytotoxicity Assay

This example describes one preferred protocol for a single cell-based fluorogenic cytotoxicity assay according to the present invention and is available in a kit (CyToxiLux®, from OncoImmunin, Inc.). Various advantages of this assay over others, e.g., $^{51}$Cr release, include: (1) cytotoxicity is measured as a fundamental biochemical pathway leading to cell death (cleavage of a cell permeable fluorogenic caspase substrate) rather than merely as the end result of cell lysis, (2) in many systems this assay is more sensitive (e.g. it could detect relatively weak CTL responses against subdominant epitopes) and more rapid, (3) cell death can be measured exclusively in target cell populations by flow cytometry or fluorescence microscopy, and (4) when combined with immunophenotypic analyses and multiparameter flow cytometry, CTL-mediated killing of primary host target cells as well as the physiology and fate of effector cells can be directly visualized and monitored.

Target cells are fluorescently labeled (red) and then coincubated with cytotoxic effector cells. At the desired time point, medium is removed from samples and replaced with a solution containing a fluorogenic caspase substrate such as those obtainable from OncoImmunin, Inc. Following incubation and washing, samples may be analyzed by flow cytometry or fluorescence microscopy. Cleavage of the substrate results in increased fluorescence in dying cells.

Components available in the CyToxiLux® kit from OncoImmunin, Inc., are listed in Table 3.

TABLE 4

Components supplied in CyToxiLux ® kit (sufficient for 50 assays).

| Components supplied in CyToxiLux ® kit (sufficient for 50 assays) | Components supplied by user |
| --- | --- |
| Vial CS (3 vials) = Caspase Substrate solution | Effector cells |
| Vial T (1 vial) = Target cell marker | Target cells |
| Staining Buffer bottle (1 bottle) | Assay Medium |

Medium A = Assay Medium. Medium in which assay will be run, i.e., medium in which target and effector cells will be coincubated.
Medium T = Target Cell Medium. Medium A plus Target cell marker. This is prepared by adding 1 µl from Vial T per ml of Medium A.

The assay is preferably performed using either 96-well plates or polypropylene microcentrifuge tubes. Microcentrifuge tubes are recommended for Target cells which adhere in culture, as re-adhesion to the 96 well plate during co-incubation with effector cells can result in sample loss.

Washing, as used in this example, refers to centrifugation followed by careful removal of all liquid from wells or tubes. Resuspension of pellets should be done with gentle pipetting of plates or tapping of tubes with finger. Do not vortex.

Target cells are prepared by suspending the target cells (suspension cells or trypsinized adherent cultures) in Medium T at $2 \times 10^6$ cells/ml. If the experimental design includes pulsing with sensitizers, e.g., peptides, they should be added to the appropriately sized Effector cell aliquots at this stage. The suspension is incubated at 37° C. for 1 hour. During this 1 hour, the effector cells can be prepared as described below At least a 10-fold volume of Medium A is added to the suspension and wash. This is repeated twice. The labeled target cells are resuspended at $2 \times 10^6$ cells/ml in Medium A. Then 100 µl of the target cell suspension is added to each assay well or tube.

Effector cells are prepared at the appropriate concentration in Medium A. For example, for a final Effector to Target ratio of 25:1 effector cells are prepared at $5 \times 10^7$ cells/ml.

The target and effector cells are coincubated as follows: 100 µl of effector cell suspension is added to each well containing target cells except at least two wells, and 100 µl of effector cell suspension is added to at least two wells that do not contain target cells. 100 µl of Medium A is added to the wells containing only targets and to wells containing only effectors to bring all samples to a final volume of 200 µl. The wells are coincubated for the desired time in the appropriate 37° C. environment, i.e., for a $CO_2$-containing medium, place in a $CO_2$-containing incubator. We recommend 1-3 hours but the exact time will depend on the cells of interest. Since this assay detects dying cells rather than cell lysis, incubation times for a given cell system should be significantly shorter than with the $^{51}$Cr release methodology.

The samples are washed and one well containing target cells only and one well containing effector cells only are resuspended with 75 µl of Staining Buffer. To all other samples add 75 µl of substrate from Vial CS. This is incubated at 37° C. for 30-60 minutes and then washed with staining buffer, resuspended in Staining Buffer. The samples are then transferred to flow cytometry tubes for analysis by flow cytometry.

Figure 6:
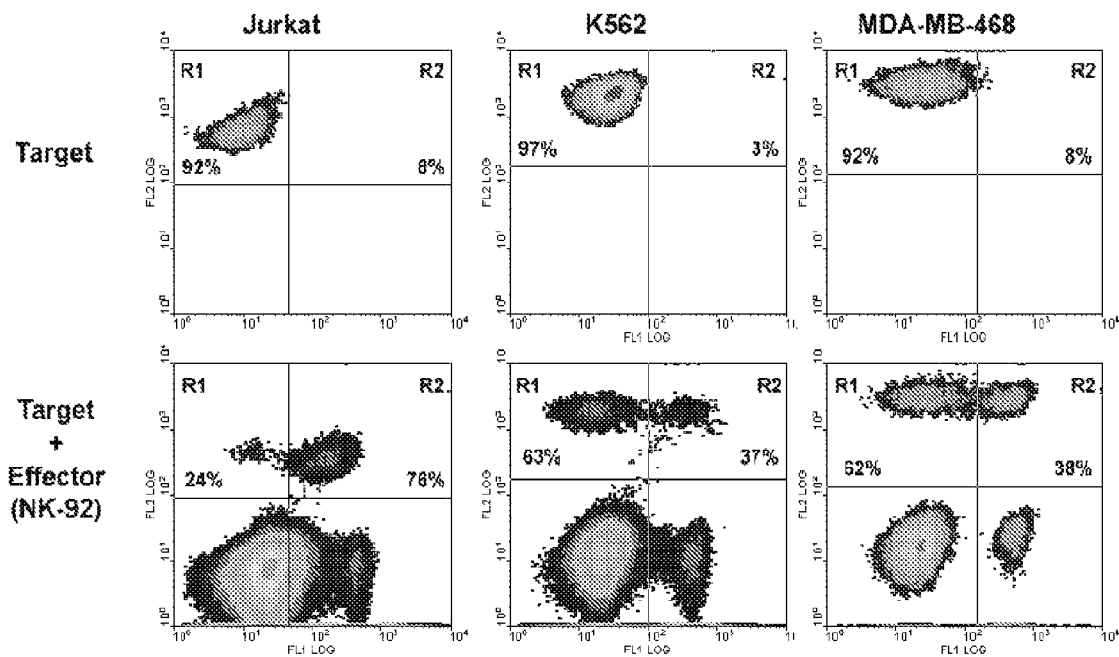
FIG. 6 shows sample flow cytometric data from an assay performed in accordance with this invention. Target cells (Jurkat, K562, or MDA-MB-468) were incubated with or without Effector cells (NK-92, 5:1 Effector:Target ratio) for 1 hour at 37° C. followed by a 45 minute incubation with the caspase substrate. Quadrants R1 (upper left of each panel) represent viable target cells while quadrants R2 (upper right) represent dying, substrate-positive target cells. Effector cells occupy the lower 2 quadrants. The percent live and dead target cells (inset % values) is calculated as R1/(R1+R2) or R2/(R1+R2), respectively. All cell lines were purchased from ATCC.

Summary of samples: A: Target cells; B: Target cells+Substrate from Vial CS; C: Target cells+Effector cells+Substrate from Vial CS (multiple samples); C: Effector cells; and D: Effector cells+Substrate from Vial CS Flow cytometry is performed as follows: Sample A is used to initially set FL1 and FL2 channels. Place the peak for cells from sample A near $10^1$ in the FL1 channel and near $10^3$ in the FL2 channel. Use sample E to setup FL2 compensation. Dead/dying Effector cells may show a high FL1×FL2 population on most single-laser flow cytometers. Compensate FL2 by FL1 until this population is on the same horizontal axis as viable Effector cells (low FL2). Use sample A to setup compensation of the FL1 channel, if necessary. Run remaining samples Sample flow cytometric data is shown in FIG. 6.

Example 6

Fluorogenic Assays Utilizing Granzyme B Substrates

Figure 7:
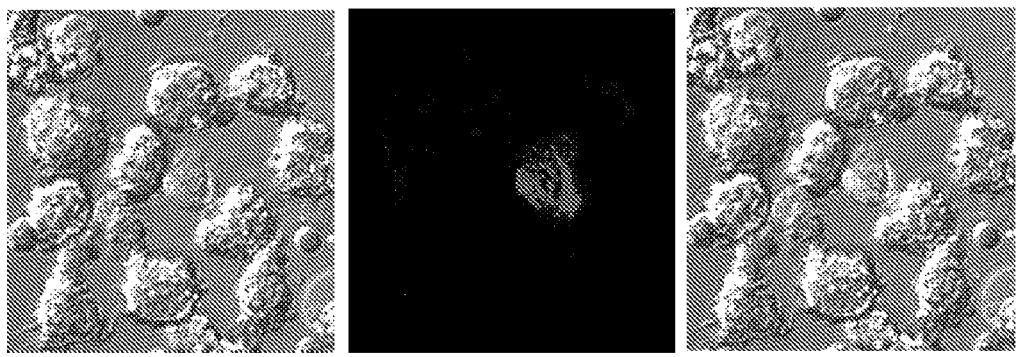
FIG. 7 shows confocal imaging of Granzyme B activity in a Jurkat cell subsequent to delivery of Granzyme B protease molecules by NK92 cell(s). Jurkat cells were prelabeled with a fluorophore which is displayed in blue prior to addition of NK92 cells (uncolored). Granzyme B activity is represented in red.

FIG. 7 shows the results of confocal imaging of Granzyme B activity in a Jurkat cell subsequent to delivery of Granzyme B protease molecules by NK92 cell(s). Jurkat cells were prelabeled with a fluorophore which is displayed in blue prior to addition of NK92 cells (uncolored). Granzyme B activity is represented in red.

Figure 8:
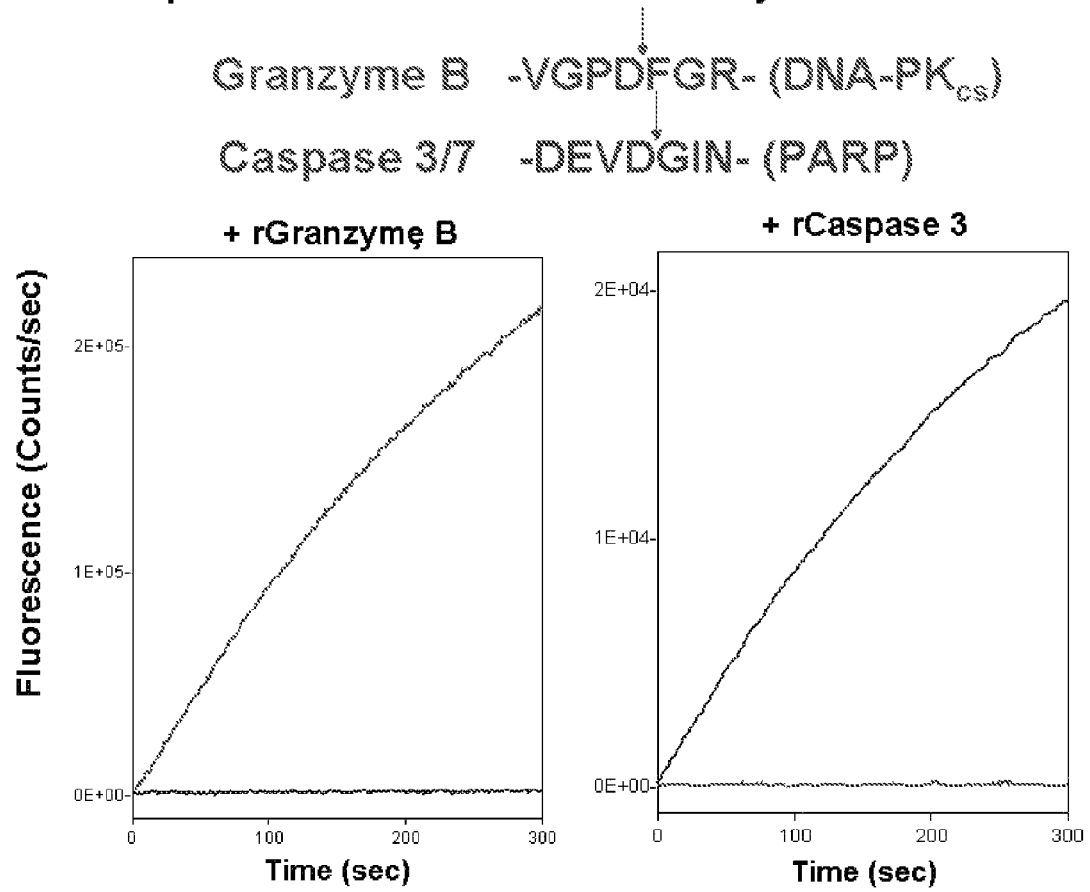
FIG. 8 illustrates selective cleavage of substrates designed for detection of Granzyme B (-VGPD'FGR- cleavage) and Caspase 3 (-DEVD'GIN- cleavage) protease activities. Fluorogenic activity of indicated substrates was measured in solution after addition of recombinant Granzyme B (left panel) and recombinant Caspase 3 (right panel).

FIG. 8 shows the selective cleavage of substrates designed for detection of Granzyme B (-VGPD'FGR- cleavage) and Caspase 3 (-DEVD'GIN- cleavage) protease activities. Fluorogenic activity of indicated substrates was measured in solution after addition of recombinant Granzyme B (left panel) and recombinant Caspase 3 (right panel).

Figure 9:
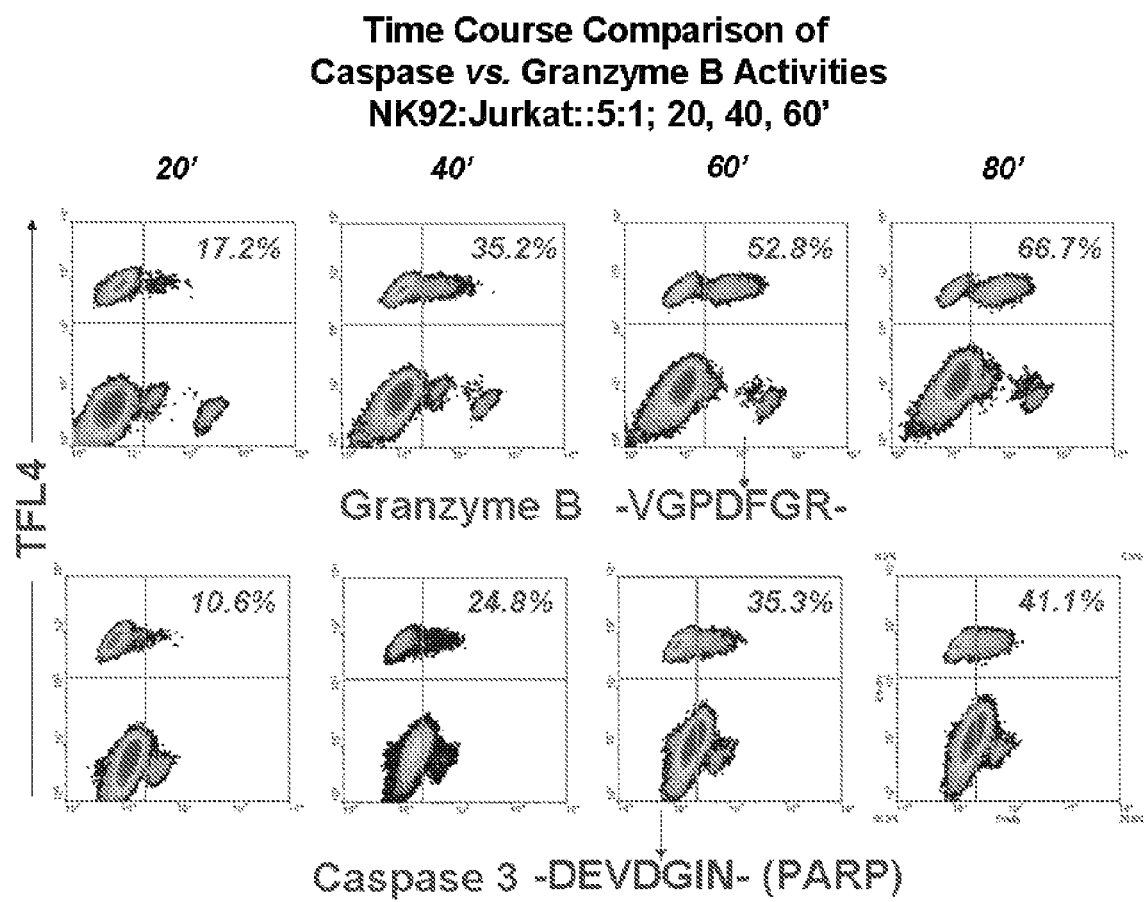
FIG. 9 show a time course comparison of caspase versus granzyme B activity.

FIG. 9 shows flow cytometric measurement of target intracellular protease activities during cell-mediated cytotoxicity. Jurkat target cells prelabeled with TLF4 were mixed with NK92 effectors at a 1:5:target:effector, centrifuged, and incubated for the indicated times (see Table 5) in the presence of the indicated substrate prior to flow cytometry. Numbers indicate percent of target cells that are positive for the indicated substrate.

TABLE 5

Percent of target cells positive for indicated substrate.

| Time (minutes) | % Granzyme B-Positive Target cells | % Caspase 3-Positive Target cells |
| --- | --- | --- |
| 20 | 17.2 | 10.6 |
| 40 | 35.2 | 24.8 |
| 60 | 52.8 | 35.3 |
| 80 | 66.7 | 41.1 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting cell-mediated cytotoxic activity, said method comprising:
providing a target cell containing a fluorescent or fluorogenic ligand that specifically binds to the substrate binding site of granzyme A or granzyme B and that produces a fluorescent signal when said ligand reacts with said granzyme;
coincubating said target cell with a cytotoxic effector cell; and
thereafter detecting an active granzyme A or granzyme B in said target cell by detecting the fluorescent signal from said ligand, and wherein the presence or activity of said activated granzyme A or granzyme B indicates that said cytotoxic effector cell is active against said target cell.

2. The method of claim 1, wherein said cytotoxic effector cell is selected from the group consisting of a cytotoxic T lymphocyte (CTL), a natural killer (NK) cell, and a macrophage.

3. The method of claim 2, wherein said cytotoxic effector cell is a cytotoxic T lymphocyte (CTL).

4. The method of claim 2, wherein said effector cell is an NK cell.

5. The method of claim 1, wherein said fluorescent or fluorogenic ligand specifically binds to the substrate binding site of granzyme B.

6. The method of claim 5, wherein said detecting occurs in a single cell.

7. The method of claim 1, wherein said fluorescent or fluorogenic ligand specifically binds to the substrate binding site of granzyme A.

8. The method of claim 7, wherein said detecting occurs in a single cell.

9. The method of claim 1, wherein said detecting comprises utilizing a single cell image based instrument.

10. The method of claim 1, wherein said detecting utilizes a flow cytometer.

11. The method of claim 1, wherein said detecting does not utilize a flow cytometer.

12. The method of claim 1, wherein said ligand comprises a granzyme B recognition domain selected from the group consisting of IEPDS (SEQ ID NO:27), VGPDFGR (SEQ ID NO:25), IEPD (SEQ ID NO:28), and VGPD (SEQ ID NO:29).

13. The method of claim 1 wherein said ligand comprises an amino acid sequence selected from the group consisting of KDPC$_5$GIEPDSGC$_5$PKGY (SEQ ID NO:12), C(S-t-Buthio)KDPC$_5$SVGPDFGRGC$_5$PKGY (SEQ ID NO:13), GKDPC$_5$SVGPDFGRGC$_5$PKGY (SEQ ID NO:14), DKDPC$_5$SVGPDFGRGC$_5$PKDDG (SEQ ID NO:15), EDGKDPC$_5$SVGPDFGRGC$_5$PKDDG (SEQ ID NO:16), KKDPC$_5$SVGPDFGRGC$_5$PKDDG (SEQ ID NO:17), KKKDPC$_5$SVGPDFGRGC$_5$PKDDG (SEQ ID NO:18), KDPC$_5$GSVGPDFGRGC$_5$PKGY (SEQ ID NO:19), C(S-tButhio)KDPC$_5$GSVGPDFGRGC$_5$PKGY (SEQ ID NO:20), and GKDPC$_5$GSVGPDFGRGC5PKGY (SEQ ID NO:21).

14. The method of claim 1, wherein said ligand is attached to a single chromophore whose fluorescence signal or whose absorption spectra is altered when said substrate is cleaved by said active granzyme.

15. The method of claim 14 wherein said ligand is attached to two fluorophores or chromophores of the same species.

16. The method of claim 14, wherein said ligand is attached to two chromophores whose fluorescence signal or whose absorption spectra is altered when said substrate is cleaved by said active granzyme.

17. The method of claim 16, wherein said chromophores form an H-dimer.

18. The method of claim 16, wherein said chromophores do not form an H-dimer.

19. The method of claim 16, wherein said chromophores are both fluorophores.

20. The method of claim 16, wherein said chromophores comprise one non-fluorescent chromophore and a fluorophore.

21. The method of claim 16, wherein said chromophores are both fluorophores and the same species of fluorophore.

22. The method of claim 1, wherein said ligand comprises a granzyme substrate having a fluorophore or chromophore at a position ranging from a P1' to a P8' residue.

23. The method of claim 22, wherein the amino terminal residue of said substrate is blocked.

24. The method of claim 22, wherein the amino terminal residue of said substrate is not blocked.

25. The method of claim 22, wherein said ligand comprises a granzyme substrate having a fluorophore attached at the P1 residue.

26. The method of claim 1, wherein said ligand comprises a fluorophore selected from the group consisting of fluoroscein, phycoerythine, carboxytetramethylrhodamine, carboxyrhodamine-X, carboxyrhodamine 110, diethylaminocoumarin, and carbocyanine dyes.

27. The method of claim 1, wherein said ligand bears a hydrophobic group.

28. The method of claim 27, wherein said hydrophobic group is a fluorophore.

29. The method of claim 27, wherein said hydrophobic group is a chromophore.

30. The method of claim 27, wherein said hydrophobic group is selected from the group consisting of Fmoc, 9-fluoreneacetyl group, 1-fluorenecarboxylic group, 9-florenecarboxylic group, and 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzenesulphonyl (Mtr), mesitylene-2-sulphonyl (Mts), 4,4'-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and trifluoroacetyl (TFA).

31. The method of claim 1, wherein said coincubating comprises fixing said target cell.

32. The method of claim 1, wherein said target or effector cells are in a histological section.

33. The method of claim 1, wherein said target cell is infected with a virus, a bacterium, or other microorganism.

34. The method of claim 1, wherein said target cell expresses a heterologous protein.

35. The method of claim 1, wherein said target cell is selected from the group consisting of a tumor cell, a neural cell, a muscle cell, a fibroblast, a connective tissue cell, a bone cell, a blood cell, a spinal fluid derived cell, a lymphatic fluid derived cell, and a cell obtained from the site of an inflammation.

* * * * *